United States Patent
Shikakubo et al.

[11] Patent Number: 6,076,255
[45] Date of Patent: Jun. 20, 2000

[54] APPARATUS FOR MANUFACTURING NEEDLE ATTACHED SUTURES

[75] Inventors: Kenji Shikakubo, Sakaimachi; Norio Yamanaka, Satte; Gennai Yanagisawa, Matsumoto, all of Japan

[73] Assignee: Kabushiki Kaisha Azwell (Azwell Inc.), Osaka-fu, Japan

[21] Appl. No.: 08/945,537

[22] PCT Filed: Feb. 13, 1997

[86] PCT No.: PCT/JP97/00378

§ 371 Date: Oct. 6, 1997

§ 102(e) Date: Oct. 6, 1997

[87] PCT Pub. No.: WO97/29691

PCT Pub. Date: Aug. 21, 1997

[30] Foreign Application Priority Data

Feb. 16, 1996 [JP] Japan ................................. 8-029229

[51] Int. Cl.⁷ ............................................. B23Q 15/00
[52] U.S. Cl. ................ 29/715; 29/407.04; 29/243.517; 83/153; 83/950
[58] Field of Search ........................ 29/407.01, 407.04, 29/712, 715, 707, 243.5, 243.517, 283.5, 515, 516, 517, 564.6, 705, 783, 788, 796; 606/224, 225, 226; 83/151, 153, 950

[56] References Cited

U.S. PATENT DOCUMENTS

| | | |
|---|---|---|
| 4,922,904 | 5/1990 | Uetake et al. . |
| 5,280,674 | 1/1994 | Granger et al. ............................ 29/516 |
| 5,417,710 | 5/1995 | Matsutani et al. ....................... 606/224 |
| 5,452,636 | 9/1995 | Rattan . |
| 5,477,609 | 12/1995 | Demarest et al. . |
| 5,485,668 | 1/1996 | Demarest et al. . |

*Primary Examiner*—David P. Bryant
*Attorney, Agent, or Firm*—Jordan and Hamburg LLP

[57] ABSTRACT

This invention relates to a needle attached suture manufacturing method and apparatus capable of cutting a suture exactly at the same length, with a simple construction and high efficiency. A transport/holding device 42 holds a suture Y and transports the suture straight forward toward a needle swaging device 20 a distance corresponding to a predetermined target value. Thereafter, the suture Y is cut at a certain position to obtain a suture strand. The suture strand is then inserted in an insertion hole formed at the end of a needle and is swaged by the needle swaging device 20. As an altered method, after the suture Y is inserted in the insertion hole of the needle, the suture Y is cut at a position away from the end of the needle a predetermined target distance.

25 Claims, 16 Drawing Sheets

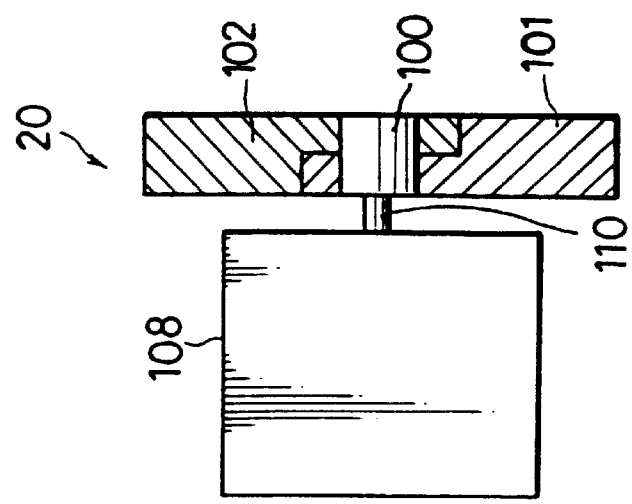
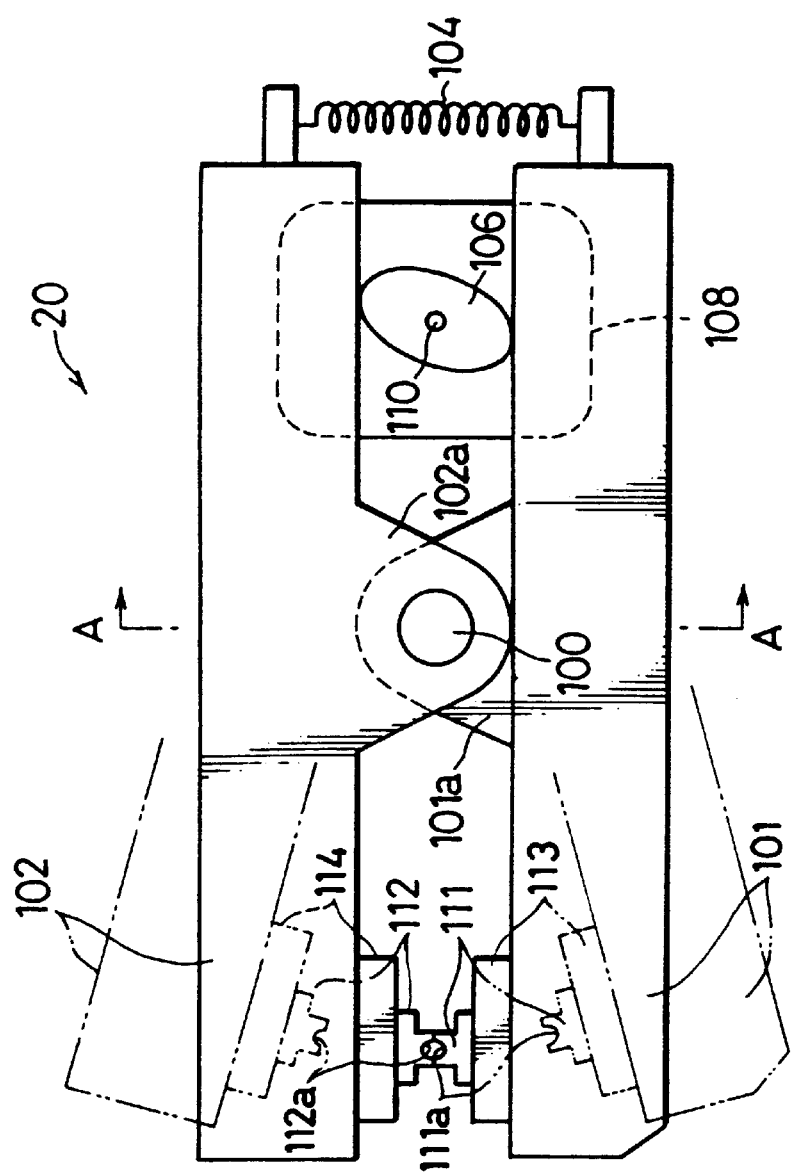
FIG. 11A
FIG. 11B

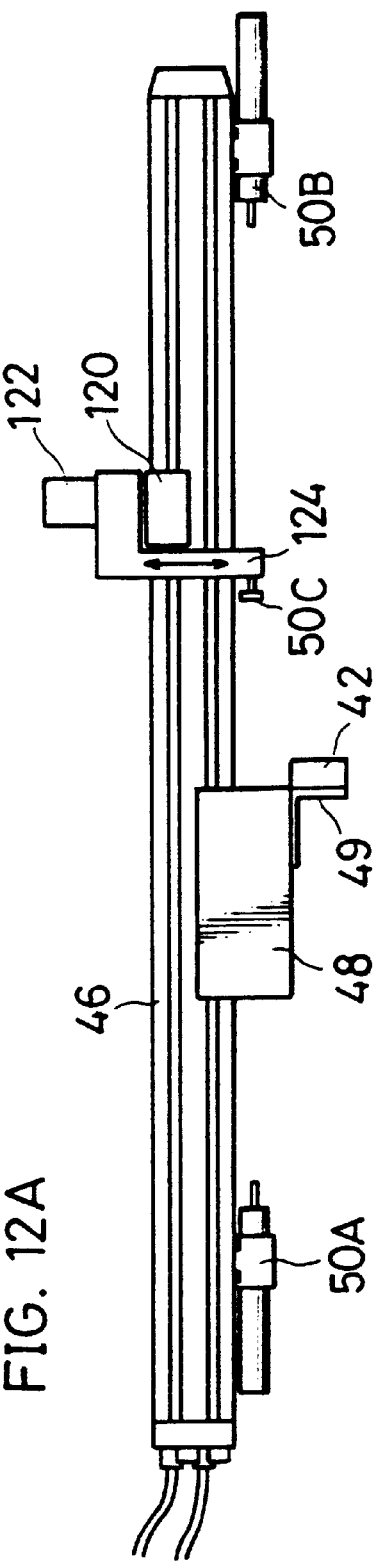
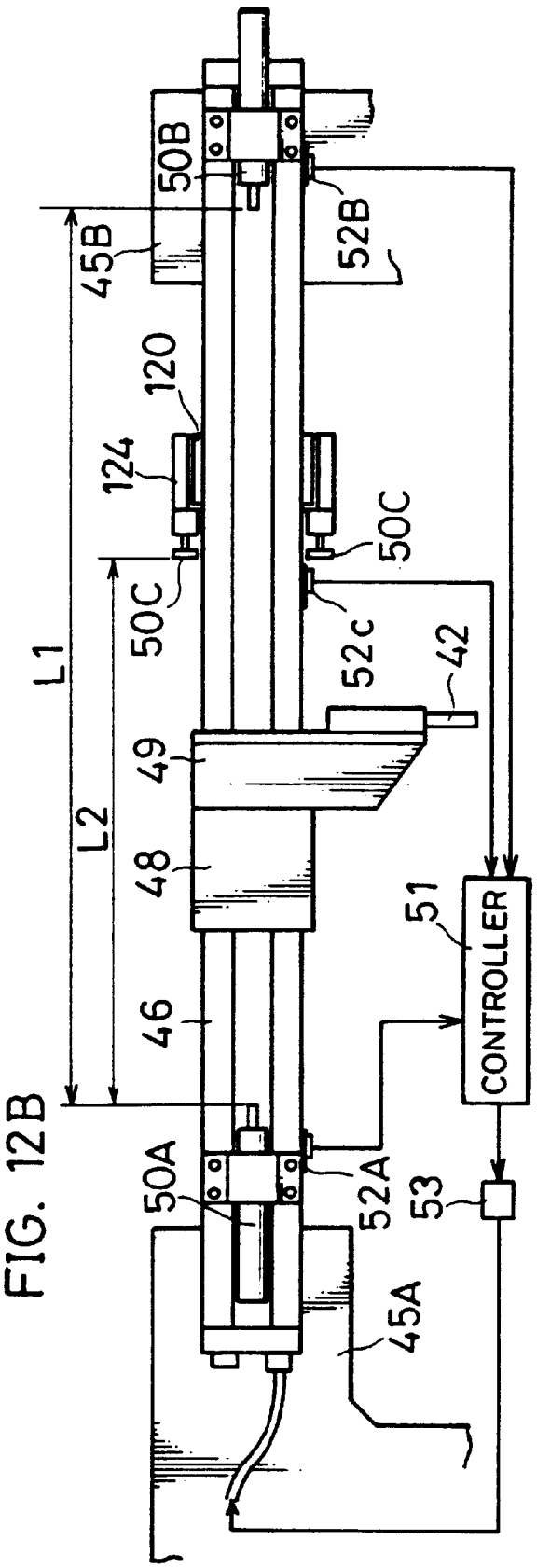
FIG. 12A
FIG. 12B

APPARATUS FOR MANUFACTURING NEEDLE ATTACHED SUTURES

BACKGROUND ART

This invention relates to a method for manufacturing needle attached sutures and an apparatus therefor, in which the end of a needle used for surgical operations and the like is swaged in a state that the lead end of a suture is inserted in an insertion hole formed in the end of the needle to combine the suture with the needle.

Recently, in the field of medical industry, there have been marketed sterilized needle attached sutures for surgical operations in which the lead end of a suture is fixedly attached to a needle. Such needle attached suture can be produced by retaining a needle in a certain orientation, and swaging the end of the needle after inserting the lead end of a suture in an insertion hole formed in the end of the needle (as disclosed in, e.g., Japanese Examined Patent Publication No. HEI 4-66579).

To produce such needle attached suture, it is required to cut a suture at a predetermined target value to obtain a suture strand of the predetermined length. Conventionally, there have been known the following methods for setting the length of the suture strand at a desired value:

A) A suture is cut into suture strands of a certain target length in advance, and then each suture strand is attached to a needle; and B) A suture wound around a bobbin or its equivalent is also wound around a brake roller mounted in a specified position along the suture feed direction. A rotational amount of the brake roller is monitored by a rotary encoder in such a manner that the brake roller stops its rotation to suspend feeding of the suture when it is confirmed that the rotational amount of the brake roller reaches a predetermined value corresponding to the target length of the suture to be cut after feeding of the suture is initiated. Upon the brake roller halting the feeding of the suture, the suture is cut at a certain position (see Japanese Examined Patent Publication No. HEI 5-11981).

In the method A), it is required to separately perform the step of cutting the suture to obtain a suture strand of the certain length and the step of combining the suture strand with a needle. In other words, the cutting step and the bonding step cannot be executed sequentially, thus resulting in a hindrance to raise production efficiency and to pursue mass production.

The method B) has involved another problem. Specifically, it is likely that the suture fed forward slips over the brake roller, resulting in a detection error of the rotary encoder which detects the feed amount of the suture. Accordingly, it is difficult to cut the suture at a desired position accurately. Furthermore, the above slippage is liable to occur as the feed speed of the suture is increased. This remarkably restricts the suture feed speed, resulting in a prolonged cycle time and lowers production efficiency.

Moreover, in the case where the target value of the suture strand is to be altered, the following steps are required. Specifically, the altered amount of feeding the suture is converted to a rotational amount detected by the rotary encoder, and a whole program for controlling the brake roller is required to be changed based on the rotational amount of the rotary encoder after conversion. In other words, this method is not feasible in quickly responding to the alteration of the target length of a suture strand.

In view of the above, an object of this invention is directed to a method and an apparatus for manufacturing needle attached sutures accurately with the same desired length, with a simple construction and high efficiency.

DISCLOSURE OF THE INVENTION

To solve the above problems, this invention has adopted the following arrangement.

This invention is directed to a method for manufacturing a needle attached suture in which an end of a needle is swaged with a lead end of a suture inserted in an insertion hole formed in the end of the needle to combine the suture with the needle, the method comprising the following steps in the order named: holding a portion near the lead end of the suture wound around a suture winding member; feeding the suture straight toward the insertion hole of the needle; suspending the feeding when a feed distance of the suture reaches a predetermined target value; cutting the suture at a predetermined position; and inserting the lead end of the cut suture in the insertion hole of the needle.

According to this method, the length of the cut suture (i.e., suture strand) becomes equal to the transport distance of the suture, as long as the suture is cut at the specified cutting position. Accordingly, the suture can be cut accurately with the same length and inserted in the insertion hole at the end of the needle following the cutting step. In the case where the length of the suture strand is to be altered, merely changing the transport distance of the suture can meet the alteration.

Further, the present invention is directed to an apparatus designed to execute the above method. Specifically, the apparatus of this invention comprises: suture winding member for winding the suture; suture holding means for holding a portion near the lead end of the suture wound around the suture winding member; transport means for transporting the suture holding means straight toward the insertion hole of the needle by a distance corresponding to a predetermined target value; and cutting means for cutting the suture at a certain position after the transport means transports the suture holding means by the predetermined distance. The apparatus is constructed such that the lead end of the suture cut by the cutting means is capable of being inserted in the insertion hole of the needle.

Preferably, the transport means may be constructed such that the predetermined target value is adjustable. Thereby, adjusting the transport distance to any desired value can obtain a suture strand of the desired length.

More preferably, the transport means may include reciprocal drive means for reciprocating the suture holding means along a predetermined transport path between two positions; end detector means for detecting the presence of the suture holding means at each position while being transported by the transport means; and transport control means for controlling the transport means to suspend the transport of the suture holding means when the end detector means detects the presence of the suture holding means. The position detected by the end detector means may be adjustable.

With this arrangement, since the distance between the positions detected by the end detector means corresponds to the transport distance of the suture holding means by the transport means, changing the distance between these positions detected by the end detector means can easily meet alteration of the cutting length of the suture.

Preferably, the apparatus may further comprise a stopper for halting the transport of the suture holding means when it is judged that the suture holding means reaches the position detected by the end detector means, and the transport halt position of the stopper may be adjustable.

More preferably, the apparatus may further comprise intermediate position detector means for detecting the presence of the suture holding means at an intermediate position between the two positions, and the transport control means may be selectable between a first mode and a second mode. The first mode is such that the transport of the suture holding means is suspended when it is judged that the suture holding means reaches the end position detected by the end detector means after feeding of the suture is initiated by the suture holding means, and the second mode is such that the transport of the suture holding means is suspended when it is judged that the suture holding means reaches the intermediate position detected by the intermediate position detector means after feeding of the suture is initiated by the suture holding means.

With this arrangement, when the first mode is selected, the suture strand of the length corresponding to the distance between the positions detected by the end detector means is obtainable. On the other hand, when the second mode is selected, the suture strand of the length corresponding to the distance between the end position detected by one of the end detector means and the intermediate position detected by the intermediate position detector means is obtainable. In other words, switching of the mode between the first mode and the second mode can automatically select the suture strand of the two different lengths.

Preferably, the suture holding means may include an intermediate stopper for changeably shifting a position between a halting position to halt the transport motion of the suture holding means when the suture holding means reaches the intermediate position detected by the intermediate position detector means, and an allowing position to allow the transport motion of the suture holding means along the transport path.

With this arrangement, when the transport control means is set at the second mode and the intermediate stopper is set to the halting position, the suture holding means can assuredly halt at the position detected by the intermediate position detector means. On the contrary, when the transport control means is set at the first mode and the intermediate stopper is set to the allowing position, the suture holding means can pass the position detected by the intermediate position detector without any obstruction.

Furthermore, the present invention is directed to a method for manufacturing a needle attached suture in which an end of a needle is swaged with a lead end of a suture inserted in an insertion hole formed in the end of the needle to combine the suture with the needle, the method comprising the following steps in the order named: holding a portion near the lead end of the suture wound around a suture winding member; feeding the suture straight toward the insertion hole of the needle; inserting the lead end of the suture in the insertion hole of the needle; and cutting the suture at a position away from the end of the needle by a predetermined target distance.

According to this method, merely changing the cutting position can adjust the length of the suture strand.

Furthermore, the present invention is directed to an apparatus for manufacturing a needle attached suture in which an end of a needle is swaged with a lead end of a suture inserted in an insertion hole formed in the end of the needle to combine the suture with the needle, the apparatus comprises: a suture winding member for winding the suture; suture holding means for holding a portion near the lead end of the suture wound around the suture winding member; transport means for transporting the suture holding means straight toward the insertion hole of the needle; and cutting means for cutting the suture after the lead end of the suture is inserted in the insertion hole of the needle. The cutting position by the cutting means is set at such a position away from the end of the needle by a predetermined target distance.

Preferably, the cutting means may be constructed such that the cutting position is adjustable. Thereby, merely changing the cutting position by the cutting means can adjust the length of the suture strand.

Preferably, the method of this invention may further comprise the step of curing a certain region of the suture near the cutting position after the feeding step and before the cutting step. Thereby, since the lead end of the suture is inserted in the insertion hole of the needle after the curing step, the suture can be smoothly inserted in the insertion hole even though the suture is composed of e.g., multi-filament.

Preferably, the apparatus may further comprise curing means for curing a certain region of the suture near the cutting position after feeding of the suture and before cutting of the suture.

More preferably, the curing means may include curing agent apply means for applying a curing agent to the suture, and conveyor means for moving the curing agent apply means in the longitudinal direction of the suture within the certain curing region.

Further, the apparatus may comprise curing agent dryer means for drying the curing agent applied by the curing agent apply means, and the conveyor means may be constructed to move the curing agent apply means and the curing agent dryer means as one piece unit in the longitudinal direction of the suture. Thereby, curing operation can be accelerated, and hence, the cycle time of producing the needle attached suture can be further shortened.

Preferably, the apparatus may further comprise holding members for holding the suture at a plural points encompassing the curing region after feeding of the suture and before cutting of the suture, and tension supplier means for providing a tension force on the suture in the holding region by the holding members by applying an external force to the suture, and the curing agent apply means may be constructed such that the curing agent is applied to the suture while being given the tension force by the tension supplier.

With this arrangement, compared to the arrangement in which the curing agent is applied to the suture without supply of a tension force to the suture, the curing agent can be applied to the suture over the certain region uniformly and smoothly. Accordingly, a variation of the diameters of the lead end of the suture can be assuredly lessened to thereby enable smooth insertion of the lead end of the suture into the insertion hole at the end of the needle.

The suture holding means may function as insertion means for inserting the suture strand into the insertion hole of the needle. Preferably, however, the apparatus may further comprise insertion means for nipping the suture held by the suture holding means after the transport means transports the suture holding means to the predetermined position, and for inserting the lead end of the suture in the insertion hole of the needle after the suture holding means releases the holding of the suture and after the cutting of the suture by the cutting means, the suture holding means operable to return to an initial position before the transport by the transport means during an insertion operation by the insertion means.

With this arrangement, the suture holding means can return to the initial position during the insertion operation by the insertion means, thus contributing to improvement of production efficiency. The insertion means may also function as insertion means for inserting the lead end of the suture before cutting into the insertion hole of the needle after the holding of the suture by the suture holding means is released.

BRIEF DESCRIPTION OF THE DRAWINGS

FIG. 11A is a front view of the needle swaging device;

FIG. 11B is a cross sectional view of the needle swaging device taken along the line A—A in FIG. 11A;

FIGS. 12A and 12B are respectively a plan view and a front view of a drive device for a transport/holding device in a second embodiment according to this invention;

BEST MODE FOR CARRYING OUT THE INVENTION

A first embodiment according to this invention is described with reference to the drawings.

Figure 1:
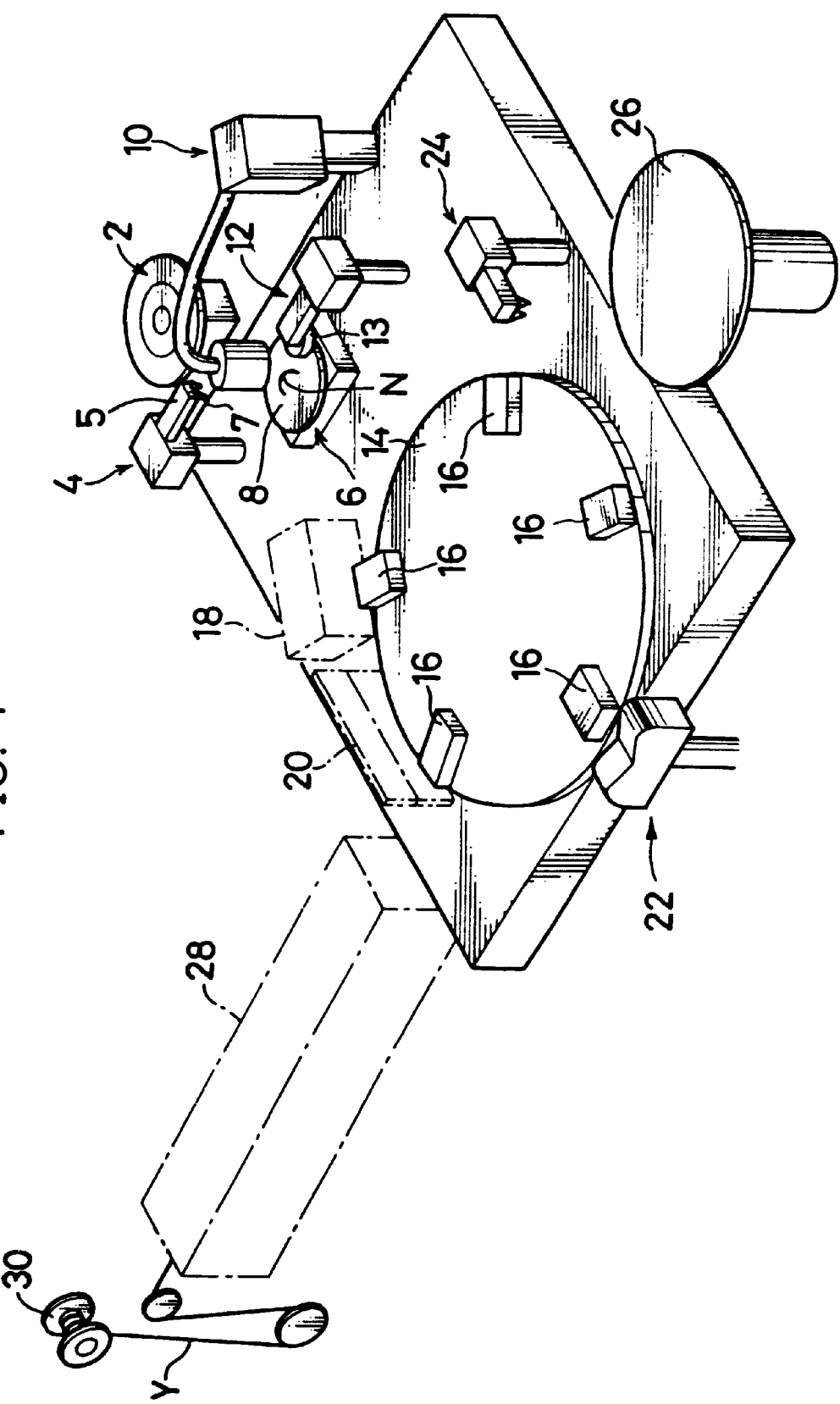
FIG. 1 is a perspective view of an entire arrangement of a needle attached suture manufacturing apparatus as a first embodiment according to this invention.
Figure 2:
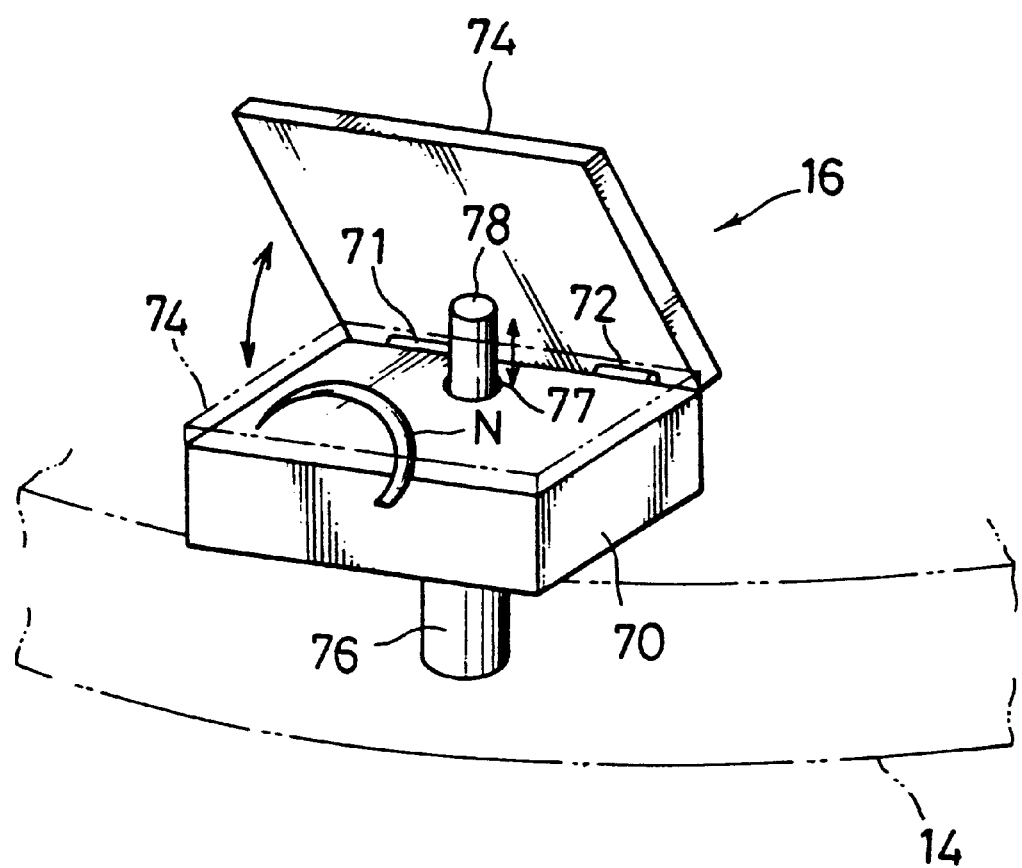
FIG. 2 is a perspective view of a needle retaining unit in the manufacturing apparatus.

FIGS. 1 and 2 show an apparatus for manufacturing needle attached sutures as the first embodiment. The apparatus comprises a needle supply device 2, a needle transport device 4, a needle orientation adjuster device 6, a needle pickup device 12, a turntable 14, a needle end adjuster device 18, a needle swaging device 20, a pull test device 22, a needle discharge device 24, a needle discharge table 26, and a suture supply device 28.

The needle transport device 4 is adapted for picking up a needle N supplied to a predetermined position on the needle supply device 2 and for transporting the same to the needle orientation adjuster device 6. Note that the needle N handled by the inventive needle attached suture manufacturing apparatus has a shape substantially curved into an arc and is formed with a suture insertion hole axially opened at the end thereof.

The needle orientation adjuster device 6 has an adjuster table 8 on which the needle N is to be placed, and an image recognizer 10 such as a CCD. The image recognizer 10 recognizes an image of the needle N placed on the adjuster table 8. The needle orientation adjuster device 6 is adapted for finely adjusting the position and the direction of the needle N placed on the adjuster table 8 to coincide the position and the direction of the recognized image with those of a target image stored in advance by horizontally moving and angularly displacing the adjuster table 8 according to needs.

The needle pickup device 12 is adapted for picking up the needle N whose position and direction have been finely adjusted on the adjuster table 8 and for supplying the same to the needle retaining unit 16 on the turntable 14.

The turntable 14 is driven to make turns on a base block and to be vertically movable, and is provided with a plural needle retaining units 16 along a circumference thereof. Each needle retaining unit 16 is provided to hold the needle N supplied from the needle pickup device 12 thereon. With an angular displacement of the turntable 14, the needle retaining unit 16 transports the needle N to the needle end adjuster device 18, the needle swaging device 20, the pull test device 22, and the needle discharge device 24 in this order.

The detailed arrangement of the needle retaining unit 16 is described with reference to FIG. 2. The needle retaining unit 16 each has a retainer main body 70 in the form of rectangular parallelepiped. The retainer main body 70 is fixedly mounted on the upper surface of the turntable 14 at an outer circumference.

An openable plate 74 is rotatably mounted on the rear side (rear side in FIG. 2) of the retainer main body 70 via hinges 71 and 72. An air cylinder 76 is arranged upright at a lower portion of the retainer main body 70. An expandable rod 78 of the air cylinder 76 is inserted in a through hole 77 formed in the middle on the rear side of the retainer main body 70. The through hole 77 is formed in the longitudinal direction of the air cylinder 76. When the air cylinder 76 is activated to cause the expandable rod 78 to move upward from the through hole 77, the openable plate 74 is pushed upward by the upper end of the expandable rod 78 to be set to an opened state (see the solid line in FIG. 2). When the air cylinder 76 is activated to cause the expandable rod 78 to be retracted in the through hole 77, the openable plate 74 is set to a closed state by the weight thereof (see the phantom line in FIG. 2).

When the openable plate 74 is opened up, the needle N transported by the needle pickup device 12 is placed on the upper surface of the retainer main body 70 in a state that the end of the needle N is jutted forward (front side in FIG. 2) from the retainer main body 70. Subsequently, when the operable plate 74 is closed, the needle retaining unit 16 securely holds the needle N therein with the end thereof jutted outward.

The needle end adjuster device 18 is adapted for pushing the end of the needle N held by the needle retaining unit 16 which is moved to a predetermined position on the turntable 14 to thereby finely adjust the end of the needle N. As will be described later, the needle swaging device 20 is adapted for swaging the end of the needle N from upward and downward in a state that a suture Y supplied from the suture supply device 28 is inserted in an insertion hole at the end of the needle N which is securely held by the needle retaining unit 16. Thereby, the suture Y and the needle N are combined with a predetermined pressing (swaging) force to produce a needle attached suture.

The suture supply device 28 is constructed such that the suture Y wound around a bobbin 30 is drawn out by a certain length and cut thereat to obtain a suture strand of the certain length and to insert the suture strand into the insertion hole of the needle N held by the needle retaining unit 16. The arrangement of the suture supply device 28 is also described later in detail.

The pull test device 22 is adapted for inspecting whether the combining strength of the suture Y and the needle N is sufficient by exerting the suture Y a tension force directing downward.

The needle discharge device 24 is provided with a needle gripper at the lead end of a pivotal arm. The needle gripper picks up the needle N (attached with the suture Y) held on the needle retaining unit 16 and discharges the needle N onto the needle discharge table 26.

The arrangement of the suture supply device 28 is described with reference to FIGS. 3 to 10 in detail.

Figure 3:
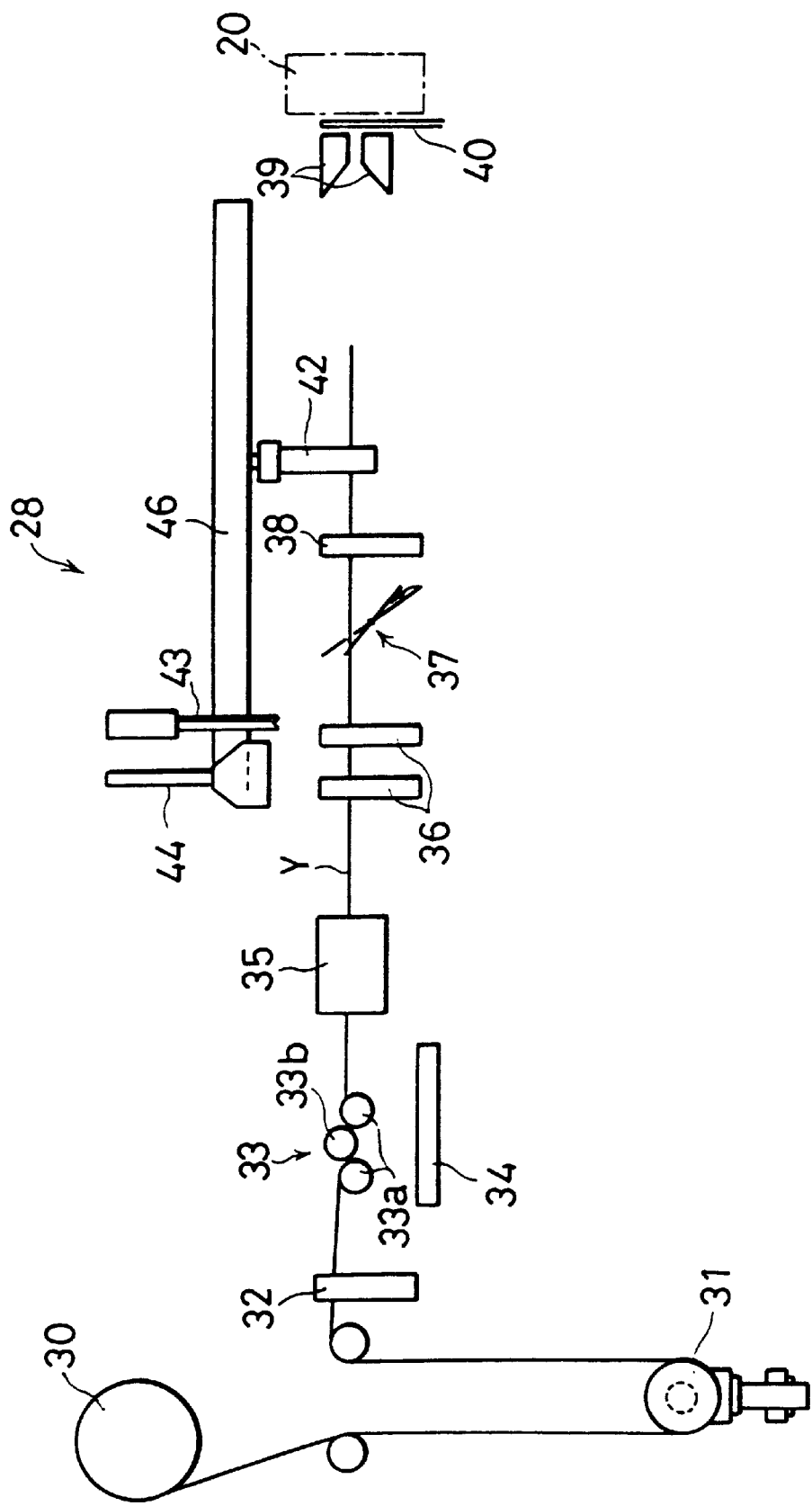
FIG. 3 is a schematic diagram showing an entire arrangement of a suture supply device in the manufacturing apparatus.
Figure 4A:
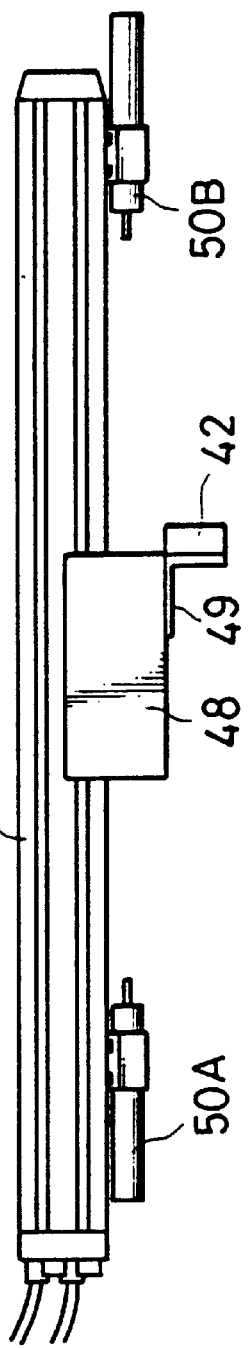
FIGS. 4A and 4B are respectively a plan view and a front view of a drive device for a transport/holding device in the suture supply device.
Figure 4B:
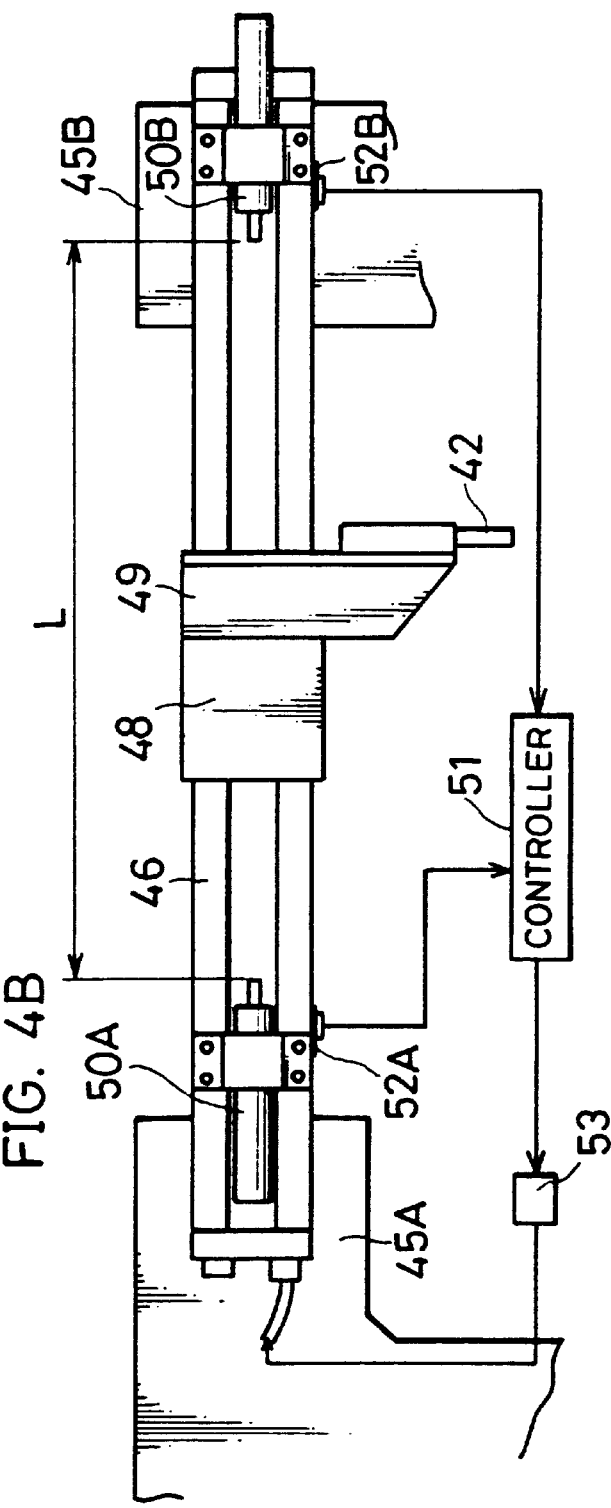

Referring to FIG. 3, the suture supply device 28 comprises, between the bobbin 30 and the swaging device 20 in this order, a dancer roller 31, a nipping device (holding means for use in applying a curing agent) 32, a tension supplier 33, electrostatic remover 34, a variation detector 35 for detecting a variation of the diameter of a suture, a pair of nipping devices 36 provided at the front and rear side with respect to the suture feed direction, a cutter 37, a nipping device (holding means for use in applying the curing agent) 38, an insertion/nipping device (insertion means) 39, and a center positioning/nipping device 40 for use in centralizing the suture.

The suture supply device 28 further comprises, in parallel with the arranging direction of the above devices, i.e., the direction of feeding (drawing out) the suture, a transport/holding device (suture holding means) 42, a curing agent apply nozzle (curing agent apply means) 43, and a dryer (curing agent dryer means) 44. The devices 42, 43, and 44 are movable in the suture feed direction.

The dancer roller 31 is mounted on the suture Y which is supplied from the bobbin 30. A weight of a certain weight hangs on the dancer roller 31 to constantly supply a certain tension force to the suture.

The holding means 32, 36, 38, and 42 nip the suture Y from the left and right direction (in FIG. 3, front and rear direction) at a certain timing. The nipping timing of the respective holding means is described later in detail.

The tension supplier 33 includes a pair of fixed rollers 33*a*, 33*a*, and a movable roller 33*b* interposed therebetween. When the movable roller 33*b* is moved down between the fixed rollers 33*a* and 33*a* to push the suture Y downward, a certain tension force is given to the suture Y.

Figure 15:
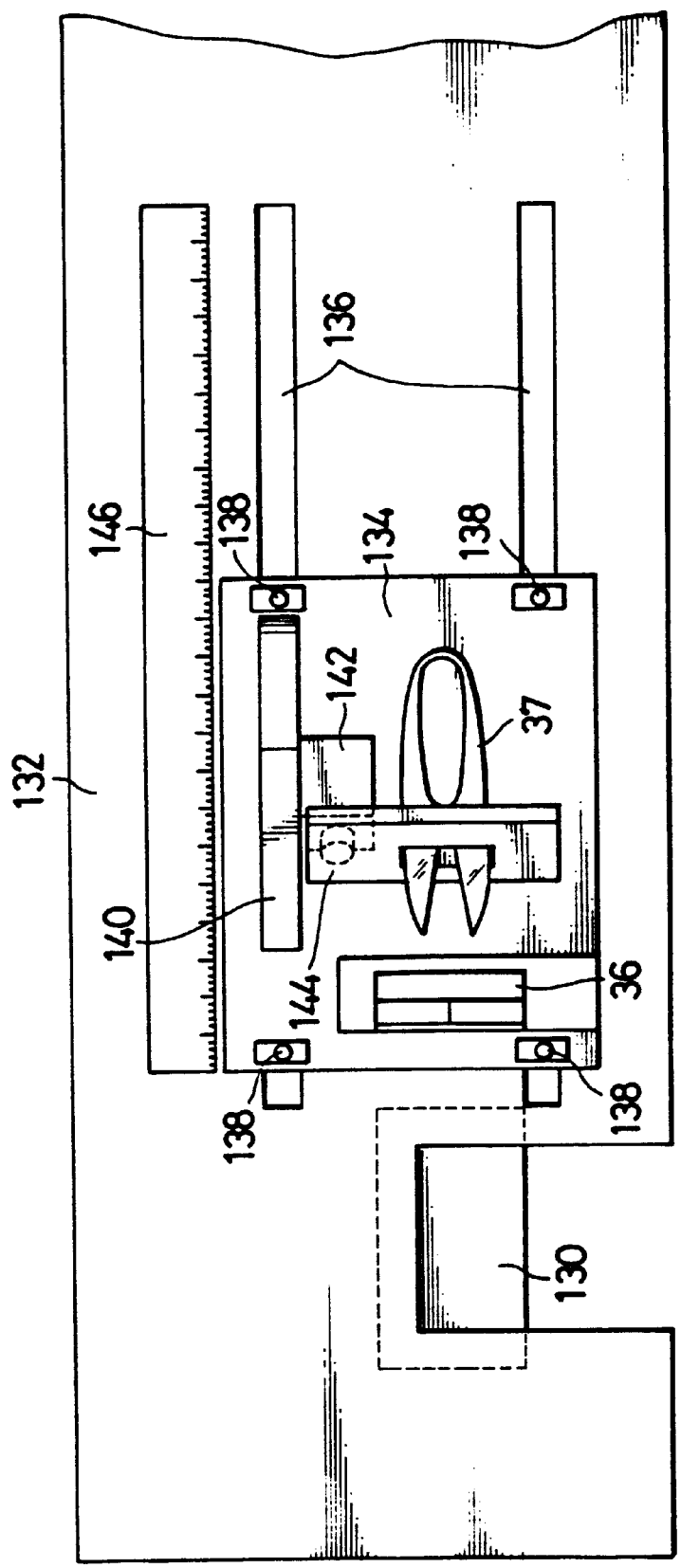
FIG. 15 is a plan view of an entire arrangement of the suture supply device in the fourth embodiment.

The cutter 37 is a pair of scissors, e.g., "oriental" scissors shown in FIG. 15, and is changeably moved to a cutting position (the position shown in FIG. 3) at which the blades of the scissors can cut the suture Y and to a retracted position at which the cutter 37 is retracted obliquely downward away from the cutting position. When the cutter 37 is operated at the cutting position, the suture Y is cut at the cutting position obliquely.

The transport/holding device 42 reciprocates within a moving range from a transport start position which is located between the nipping devices 36 and 36, and a transport end position which is away from the transport start position by a certain distance toward the needle swaging device 20 (distance corresponding to a target length at which the suture Y is to be cut). A drive device for reciprocating the transport/holding device 42 is described next in detail with reference to FIGS. 4A and 4B.

The reciprocal movement drive device for the transport/holding device 42 has a rodless cylinder 46 (a cylinder without a rod) extending in the suture feed direction. The rodless cylinder 46 is activated when air is supplied thereto through an air intake valve 53 to move a movable block 48 linearly straight toward the needle swaging device 20 in the extending direction of a main body of the cylinder 46. The transport/holding device 42 is mounted on the movable block 48 via a bracket 49.

The rodless cylinder 46 is further provided with shock absorbers 50A and 50B at a position corresponding to the opposite ends of the reciprocal moving range of the transport/holding device 42 to prohibit a further movement of the movable block 48 beyond the moving range. Sensors (end detector means) 52A and 52B are provided respectively at such a position as to detect a contact of the movable block 48 with the shock absorbers 50A and 50B. Specifically, the shock absorber 50A (or sensor 52A) is disposed away from the shock absorber 50B (or sensor 52B) by the distance corresponding to the target length of the suture Y.

The shock absorbers 50A, 50B and the sensors 52A, 52B each are fixedly attached to the rodless cylinder 46 by means of bolt or its equivalent. With this arrangement, these members can be detachably attached to the rodless cylinder 46 at any desired position.

A detection signal outputted from the sensors 52A and 52B is transmitted to a controller 51 such as a microcomputer. The controller 51 outputs a control signal to the air intake valve 53 based on the detection signal from the sensors 52A and 52B to control an operation of the rodless cylinder 46. The controller 51 also sequentially controls various operations of the elements constituting the suture supply device 28 such as the holding means 32, 36, and 38.

The curing agent apply nozzle 43 moves a certain range between the cutting position of the cutter 37 and a position toward the nipping device 36 by a certain distance away from the cutting position. While moving within the curing agent apply range, the curing agent apply nozzle 43 applies a curing agent such as an adhesive agent to the surface of the suture Y. The dryer 44 is adapted for blowing heated air onto the curing agent coated on the surface of the suture Y to dry the coated curing agent.

Figure 5:
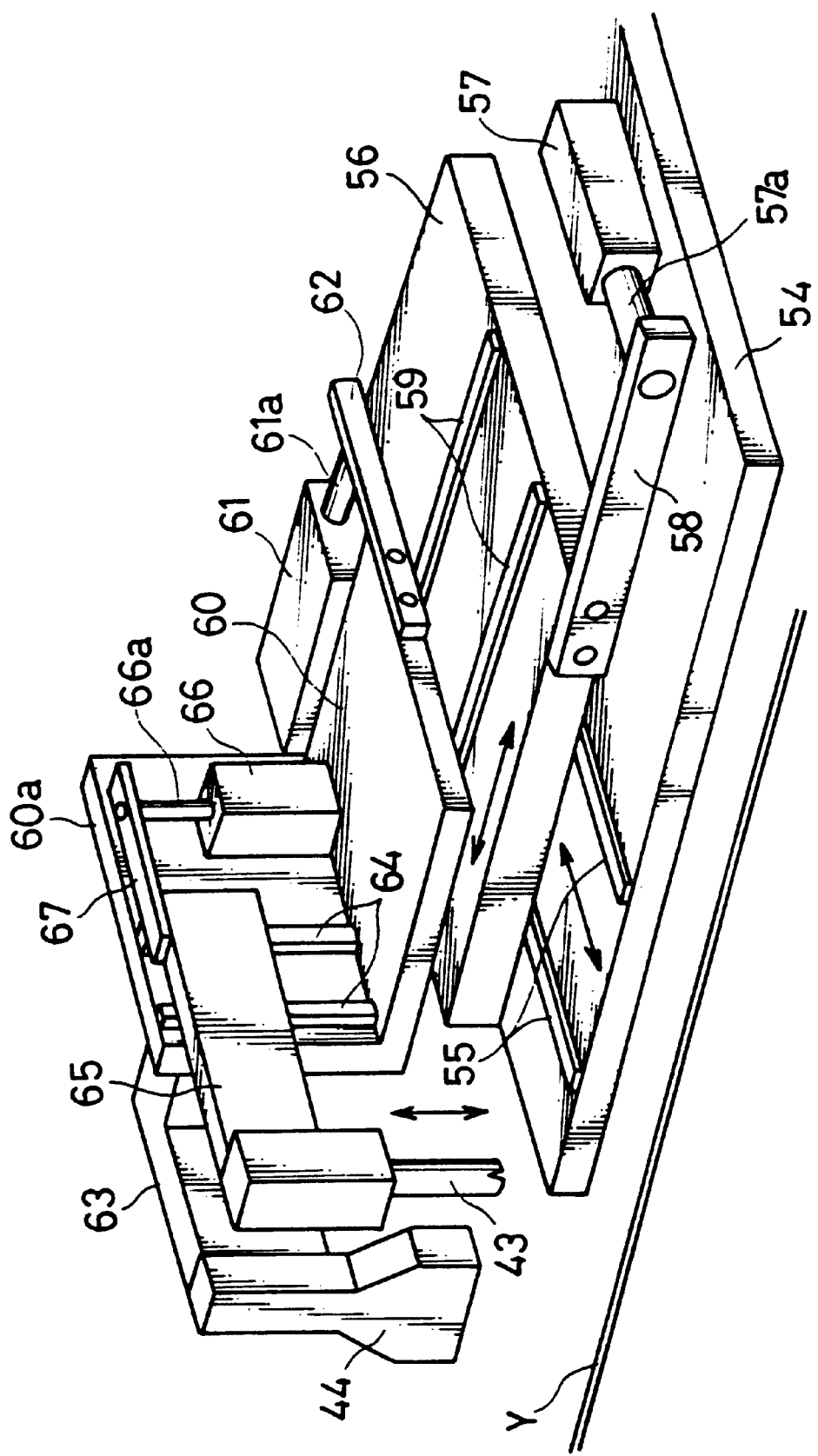
FIG. 5 is a perspective view of a conveyor device for transporting a curing agent apply nozzle in the suture supply device.

The curing agent apply nozzle 43 and the dryer 44 are transported by conveyor means shown in FIG. 5 in respective directions. In FIG. 5, a support plate 54 is fixedly disposed obliquely, while maintaining the horizontal posture.

A movable plate 56 is mounted slidably along a pair of rails 55 provided on the horizontal member 54 forward and backward (in FIG. 3, front and rear direction). An air cylinder 57 is fixedly mounted on the support plate 54 and is connected to the movable plate 56 via a connecting member 58 and an expandable rod 57*a*. When the air cylinder 57 is expanded and contracted, the movable plate 56 is slidably moved forward and backward.

Similarly, a pair of rails 59 are provided on the movable plate 56 extending in forward and backward direction (in FIG. 3, right and left direction). A movable plate 60 is mounted slidably along the rails 59 forward and backward. An air cylinder 61 is fixedly mounted on the movable plate 56 and is connected to the movable plate 60 via a connecting member 62 and an expandable rod 61a. In accordance with an expansion and a contraction of the air cylinder 61, the movable plate 60 is slidably moved forward and backward direction.

The movable plate 60 is formed with an upright wall 60a extending vertically upward. A support arm 63 extends from one side of the upright wall 60a, and the dryer 44 is fixedly mounted on the lead end of the support arm 63. At the opposite side of the upright wall 60a, there is fixedly mounted a pair of rails 64 along which a movable plate 65 is vertically movable. An air cylinder 66 is fixedly mounted on the upright wall 60a and is connected to the movable plate 65 via a connecting member 67 and an expandable rod 66a. The curing agent apply nozzle 43 is fixedly-mounted at the lead end of the movable plate 65. When the air cylinder 66 is expanded and contracted, the movable plate 65 and the curing agent apply nozzle 43 are integrally moved up and down.

With this arrangement, in accordance with a movement of the movable plate 56 with respect to the support plate 54, the curing agent apply nozzle 43 and the dryer 44 are integrally transported horizontally between a vertically aligned position at which these devices 43 and 44 are located just above the suture Y and a retracted position at which the devices 43 and 44 are horizontally retracted from the vertically aligned position.

Figure 6A:
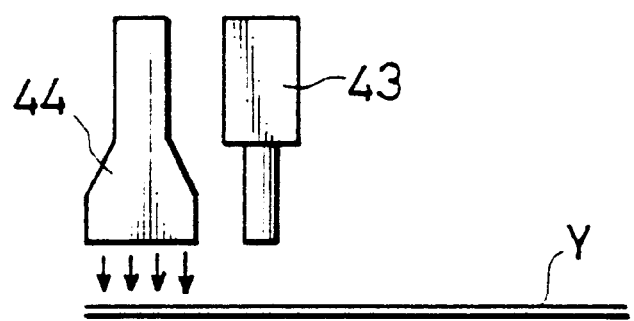
FIGS. 6A to 6D are front views showing a series of curing agent apply operations conducted by the curing agent apply nozzle.
Figure 6B:
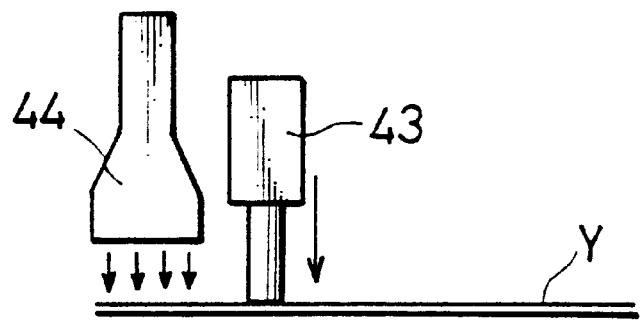
Figure 6C:
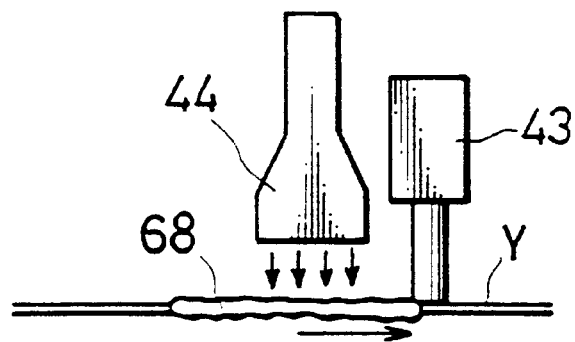
Figure 6D:
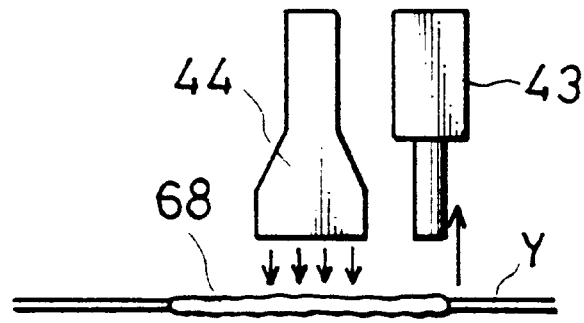

Next, when the movable plate 60 is moved in the specified direction with respect to the movable plate 56, the nozzle 43 and the dryer 44 are transported from the curing agent apply start position shown in FIGS. 6A and 6B to the curing agent apply finish position shown in FIGS. 6C and 6D along the longitudinal direction of the suture Y. Further, the movable plate 65 is moved upward and downward with respect to the movable plate 60. In accordance with the up and down movement of the movable plate 65, the nozzle 43 is moved up and down independently of the dryer 44 between a retracted position above the suture Y as shown in FIGS. 6A and 6D and a contact position at which the nozzle 43 substantially comes into contact with the suture Y, as shown in FIGS. 6B and 6C.

The insertion/nipping device 39 is disposed at such a position as to vertically nip the suture Y. At a rear end (left end portion in FIG. 10) of the insertion/nipping device 39, there is formed a tapered portion 39a with the size thereof increased as approaching toward the rear end thereof. The tapered portion 39a is provided to smoothly guide insertion of the suture Y from the rear end.

Figure 7:
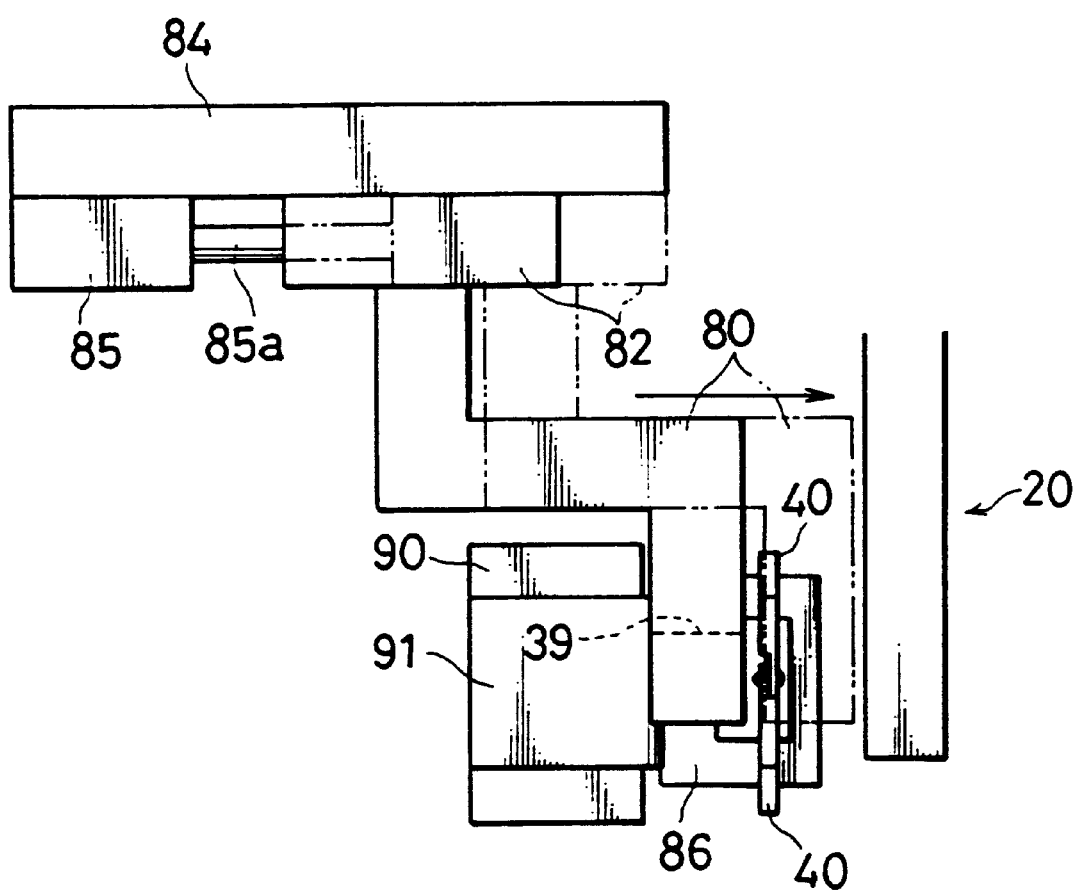
FIGS. 7 and 8 are respectively a plan view and a front view showing drive devices for use in inserting a suture and positioning the center of the suture while nipping the suture in the manufacturing apparatus.
Figure 8:
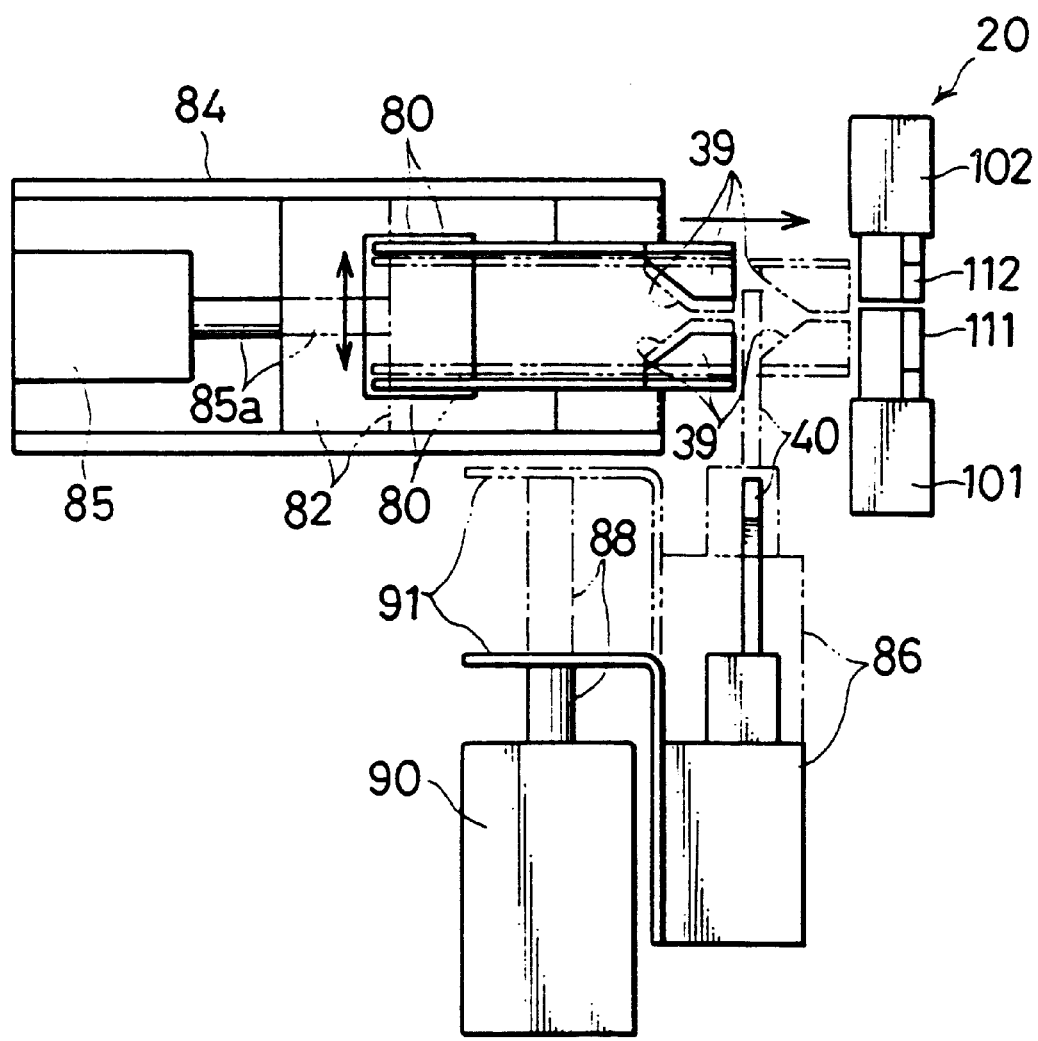

The insertion/nipping device 39 is driven by an insertion/nipping drive device shown in FIGS. 7 and 8. Upper and lower nipping portions of the insertion nipping/device 39 are fixed to the lead end of a pair of upper and lower support plates 80 and 80, respectively. The base end of the upper and lower support plates 80 and 80 is mounted on a clamp 82. The clamp 82 is internally provided with an air cylinder (not shown) for moving the upper and lower support plates 80 and 80 toward and away from each other. The insertion/nipping device 39 is changed to a nipping position at which the upper and lower nipping portions vertically nip the suture Y and a release position at which the nipping state is released in response to a movement of the upper and lower support plates 80 and 80.

The clamp 82 is supported on a base member 84 to be slidable in the direction parallel to the longitudinal direction of the suture Y (left and right direction in FIGS. 7 and 8). An air cylinder 85 is fixed to the base member 84 horizontally. The clamp 82 is connected to the air cylinder 85 via an expandable rod 85a. When the air cylinder 85 is expanded and contracted, the clamp 82 reciprocates between the position shown by the solid line in FIG. 7 and the position shown by the phantom line in FIG. 7. The solid-line position corresponds to a suture receiving position of the insertion/nipping device 39 at which the device 39 can receive a portion near the lead end of the suture Y which has been carried by the transport/holding device 42 for nipping, while the phantom-line position corresponds to a suture insertion position of the device 39 at which the lead end of the suture Y nipped by the insertion/nipping device 39 can be inserted in an insertion hole formed in the end of the needle N which is held by the needle retaining unit 16.

The center positioning/nipping device 40 is provided between the insertion/nipping device 39 and the needle swaging device 20, and is connected to an air cylinder 86 at the lower end thereof. In accordance with an operation of the air cylinder 86, the center positioning/nipping device 40 is changed to a nipping position at which left and right nipping portions of the device 40 nip the suture Y from leftward and rightward directions as shown by the phantom line in FIG. 9, and a release position at which the nipping state is being released as shown by the solid line in FIG. 9. When the center positioning/nipping device 40 is set to the nipping position to nip the lead end of the suture Y, the suture Y is assuredly positioned in the center of the insertion hole (i.e., position at which the lead end of the suture Y can be inserted in the insertion hole of the needle N).

The air cylinder 86 is connected to an expandable rod 88 of an air cylinder 90 via a bracket 91. When the air cylinder 90 is expanded and contracted, the center positioning/nipping device 40 is changed to an uppermost position (shown by the phantom line in FIG. 8) at which the device 40 is operable to horizontally nip the suture Y and a lowermost position (shown by the solid line in FIG. 8) at which the device 40 is retracted below the suture Y.

The detailed arrangement of the needle swaging device 20 is described with reference to FIGS. 9 to 11. The needle swaging device 20 has a horizontal pin 100 supported on a base member via an unillustrated support member, a lower die support member 101, and an upper die support member 102 extending horizontally. The lower die support member 101 is formed with a projection 101a projecting upward from the upper surface in the middle with respect to the left and right direction thereof in FIG. 11A, and the upper die support member 102 is formed with a projection 102a projecting downward from the underside in the middle with respect to the left and right direction thereof in FIG. 11A. The upper die support member 102 and the lower die support member 101 are rotatably supported about the horizontal pin 100 (i.e., set to an opened and closed state) in a state that the horizontal pin 100 is horizontally fitted in a hollow of the projections 101a and 102a.

One end (in FIG. 11A, right end) of the lower die support member 101 is connected to that of the upper die support member 102 via a tension spring 104. A cam 106 is interposed between the lower die support member 101 and the upper die support member 102, and is linked to an output shaft 110 of a cam drive motor 108. The cam 106 is configured such that the lower and upper die support members 101 and 102 are pivotally rotated in the opposite direction about the horizontal pin 100 in accordance with a rotation of the cam 106 by the cam drive motor 108 to move toward and away from each other.

On the upper surface at the opposite end (left end portion in FIG. 11A) of the lower die support member 101, there is mounted a lower swaging die 111 in an upright posture via a die support block 113. On the underside surface at the opposite end (left end portion in FIG. 11A) of the upper die support member 102, there is mounted an upper swaging die 112 via a die support block 114, as opposed to the lower swaging die 111. In the middle of the upper end of the lower swaging die 111, there is formed a semicircular cutaway 111a whose diameter is smaller than the diameter of the end of the needle N. Similarly, in the middle of the lower end of the upper swaging die 112, there is formed a semicircular cutaway 112a whose diameter is smaller than the diameter of the end of the needle N.

When the lower and the upper die support members 101 and 102 are set to a closed state as shown by the solid line in FIG. 11A, the end of the needle N held by the needle retaining unit 16 is swaged while being pressingly interposed between cutaways 111a and 112a of the lower and upper swaging dies.

On a side (left side in FIG. 10) of the lower swaging die 111 and the die support block 113 on which the suture Y is to be inserted, there is fixedly and integrally mounted a suture guide plate 95. Similarly, on a side of the upper swaging die 112 and the die support block 114 on which the suture Y is to be inserted, there is fixedly and integrally mounted a suture guide plate 96. In the middle of the upper end of the lower guide plate 95 and in the middle of the lower end of the upper guide plate 96, there are respectively formed semi-conical guide holes 95a and 96b whose radius is lessened in the suture insertion direction. The diameter of the guide holes 95a and 96b on the side of the swaging dies 111 and 112 is set slightly larger than the diameter of an insertion hole 116 formed in the end of the needle N.

An operation of the needle attached suture manufacturing apparatus according to this invention is described in the following.

Referring to FIG. 1, the needle N supplied to the predetermined position on the needle supply device 2 is transported to the predetermined position on the adjuster table 8 of the needle orientation adjuster device 6 by the needle transport device 4, and is placed thereat.

The image recognizer 10 recognizes an image of the needle N placed on the adjuster table 8, and the adjuster table 8 is moved in the respective directions so as to coincide the direction and the position of the recognized image, with those of the target image which are stored in advance. Thereafter, the needle whose direction and position have been adjusted by the movement of the adjuster table 8 is picked up by the needle pickup device 12 and carried to the needle retaining unit 16 on the turntable 14.

When the needle is about to be carried to the needle retaining unit 16, the air cylinder 76 shown in FIG. 2 is expanded to push up the openable plate 74, thereby exposing the upper surface of the retainer main body 70 outside. Then, the needle N is placed on the retainer main body 70 in a state that the end of the needle N is jutted outward from the retainer main body 70. Thereafter, the air cylinder 76 is contracted to close the openable plate 74 by the weight thereof, thereby allowing the needle N to be retained by the needle retaining unit 16. In this state, the turntable 14 is rotated to a specified angular position. Thereby, the needle retaining unit 16 carrying the needle N is transported to the needle end adjuster device 18, where the end of the needle N is pushed to a certain position to finely position the end of the needle. Thereafter, the turntable 14 is angularly displaced to transport the needle retaining unit 16 carrying the needle N to the needle swaging device 20.

When the needle N is carried to the needle swaging device 20, as shown by the phantom line in FIG. 11A, the upper swaging die 112 and the lower swaging die 111 are opened up away from each other to define a large opening. In this state, the turntable 14 is rotated to a certain angular position to transport the end of the needle N in the opening between the upper and lower swaging dies 112 and 111.

In the meantime, the suture supply device 28 shown in FIG. 3 conducts the following steps of cutting the suture Y to obtain a suture strand of a certain length, supplying the suture strand to the needle swaging device 20, and inserting the lead end of the suture strand in the insertion hole 116 of the end of the needle N.

1) The holding means 32 and 38 hold the suture Y. The tension supplier 33 supplies a certain tension force to the suture Y between the holding means 32 and 38.

2) The curing agent apply nozzle 43 and the dryer 44 shown in FIG. 5 are integrally moved forward with the movable plates 56 and 60 by an extension of the air cylinder 57 from the retracted position to the vertically aligned position right above the suture Y (see FIG. 6A). Subsequently, when the air cylinder 66 is set to a contracted state, the movable plate 65 is lowered to render the lead end of the nozzle 43 in contact with the suture Y (see FIG. 6B). Thereupon, the air cylinder 61 is expanded to transport the nozzle 43 and the dryer 44 from the curing agent apply start position toward the predetermined position at which the suture Y is to be cut by the cutter 37 (see FIG. 6C).

During conveyance of the nozzle 43 and the dryer 44, a curing agent 68 supplied from the nozzle 43 is coated on the surface of the suture Y, while the dryer 44 blowing heated air onto the coated surface of the suture Y following the nozzle 43. Thereby, curing of the curing agent 58 is accelerated. At this time, since the certain tension force is supplied to the suture Y, the curing operation of the suture Y with the reduced diameter thereof can be performed, thereby performing a desirable curing operation. After the coating of the curing agent is finished, the nozzle 43 is raised upward, and then returns to the retracted position together with the dryer 44 (see FIG. 6D).

3) Subsequently, the nipping devices 36 and 36 hold the suture Y, and the cutter 37 cuts the suture Y at the predetermined cutting position. At the same time of cutting operation, the nipping devices 32 and 38 release holding of the suture Y.

4) At this time, the transport/holding device 42 is located at the position where the movable block 48 shown in FIG. 4 comes into contact with the shock absorber 50A (i.e., position detected by the sensor 52A). In other words, the transport/holding device 42 holds the suture Y at the position between the nipping devices 36 and 36 (transport start position). At this time, the lead end position of the suture Y corresponds to the cutting position by the cutter 37 in the previous cutting operation. Accordingly, the transport/holding device 42 holds a portion near the lead end of the suture Y. Note that, at this time, the lead end of the suture Y has already been coated with the curing agent 68.

5) After the nipping devices 36 and 36 release holding of the suture Y, the rodless cylinder 46 is activated to transport the transport/holding device 42 together with the movable block 48 linearly straight toward the needle N (which is held by the needle retaining unit 16). Upon reaching the position in contact with the shock absorber 50B, the movable block 48 is detected by the sensor 52B. A detection signal indicative of the presence of the movable block 48 at the shock absorber 50B is transmitted to the controller 51. Thereby, driving of the rodless cylinder 46 is suspended, and the movable block 48 and the transport/holding device 42 stay at the position detected by the sensor 52B. With this operation, the suture Y is exactly fed by the dimension corresponding to the distance L between the shock absorbers 50A and 50B. In this way, the above operations 1) to 5) are repeated by a certain number of times to obtain suture strands exactly with the predetermined target length (=L).

After the transport/holding device 42 reaches the position in contact with the shock absorber 50B, the center position/nipping device 40 is set to the nipping position to thereby position the center of the lead end of the suture to be inserted. Subsequently, the suture strand whose center is aligned with the insertion hole of the needle is held by the insertion/holding device 39. After the holding by the insertion/holding device 39, the transport/holding device 42 releases the suture Y, and returns to the initial position between the nipping devices 36 and 36 (transport start position shown in the step 4)). Upon returning of the transport/holding device 42 to the initial position, the center positioning/holding device 40 releases the suture Y and then moves to the retracted position below the suture Y.

Figure 9:
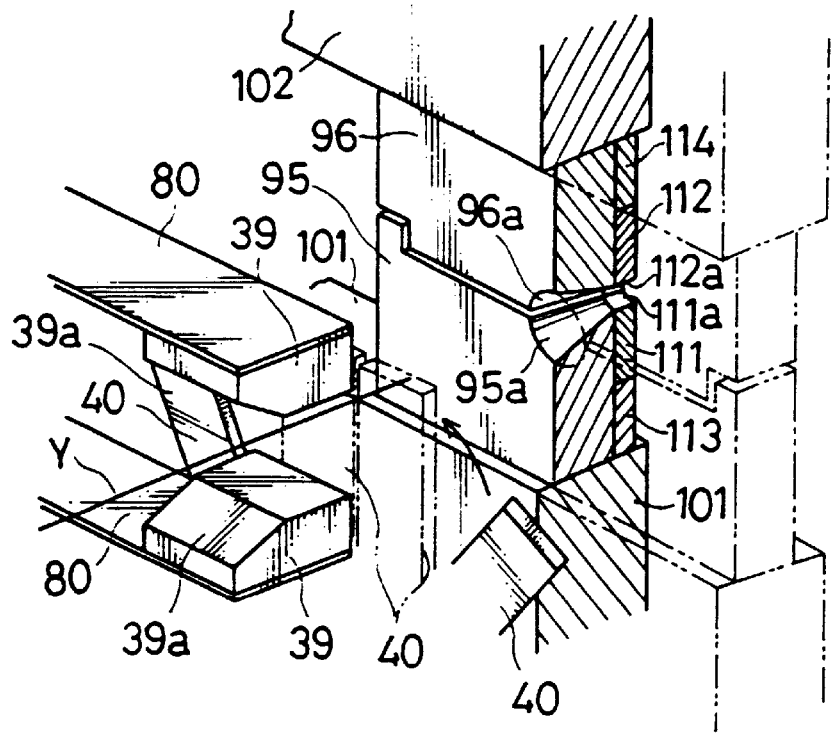
FIG. 9 is a partially cross sectional perspective view showing a positional relationship between the insertion/nipping device, center positioning/nipping device, and a needle swaging device.
Figure 10:
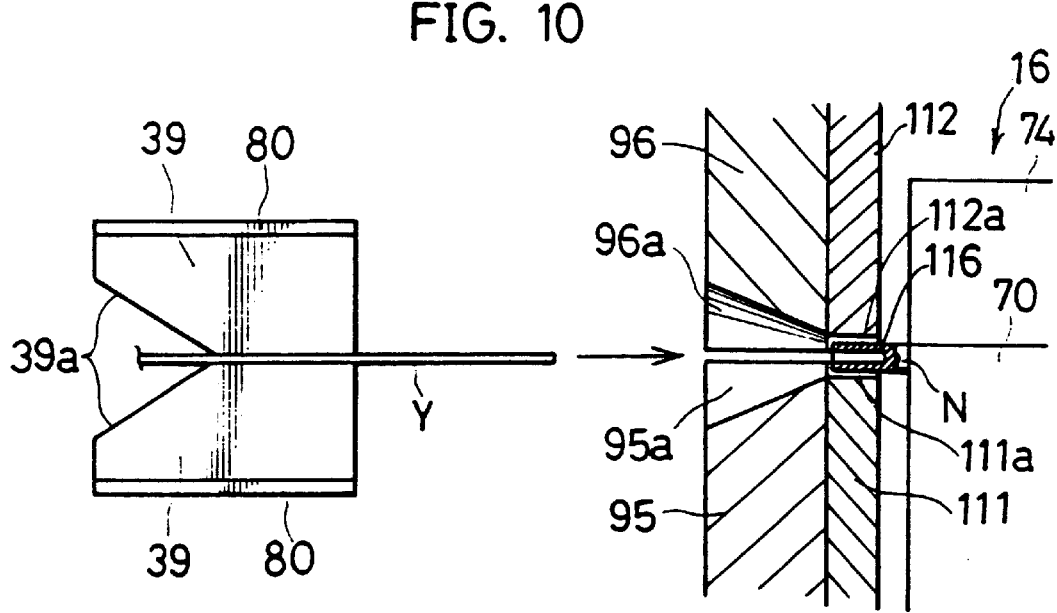
FIG. 10 is a partially cross sectional front view showing the positional relationship of the devices in FIG. 9.

Referring to the needle swaging device 20, the cam 106 is rotated, and the upper swaging die 112 and the upper guide plate 96, and the lower swaging die 111 and the lower guide plate 95 move toward each other to set the cutaway 111a of the swaging die 111 and the cutaway 112a of the swaging die 112 substantially in contact with the outer circumference of the end of the needle N (state shown by FIGS. 9 and 10). In this state, when the insertion/holding device 39 holding the suture Y proceeds forward (to the suture insertion position) in the direction of arrow shown in FIG. 10 from the position (suture receiving position) shown in FIGS. 9 and 10, the lead end of the suture Y is inserted in the insertion hole 116 at the end of the needle N which is held by the needle retaining unit 16.

At this time, the lead end of suture Y has already been coated with the curing agent 68, and has the center positioned by the center positioning/nipping device 40. Further, the tapered guide holes 95a and 96a of the guide plates 95 and 96 smoothly guide the insertion of the lead end of the suture strand into the insertion hole 116 of the needle N.

In this embodiment, the inserting step is conducted after the cutting step.

After the inserting step, the cam 106 is rotated further in the same direction to move the swaging dies 111 and 112 further toward each other, thereby fastening the end of the needle N with a certain swaging force. Thus, the end of the needle is swaged with the suture to fixedly attach the lead end of the suture to the needle N to produce a needle attached suture. After the swaging is finished, the swaging dies 111 and 112 are moved away from each other to the respective initial positions to define a large opening. Then, the turntable 14 is rotated to a certain angular position to transport the needle N on the needle retaining unit 16 to the pull test device 22.

The pull test device 22 confirms whether the swaging strength is sufficient by exerting a certain stationary load to the suture Y which is fixedly attached to the needle N in a state that the needle retaining unit 16 retains the needle N. The needle attached suture which passed the inspection of the pull test device 22 (i.e., needle attached suture in which the suture Y did not pull out from the needle during the test of giving the stationary load) is carried to the needle discharge device 24 by a further rotation of the turntable 14. Then, a pickup operation and a pivotal rotation of the needle discharge device 24 discharges the needle attached suture onto the needle discharge table 26.

According to the method and apparatus of this invention, the suture Y can be cut exactly at the same length corresponding to the transport stroke of the transport/holding device 42 (i.e., the distance L between the shock absorbers 50A and 50B) to obtain suture strands of the same length, and these suture strands of the certain length can be efficiently combined with the needle N. Further, the length of the suture strand can be altered merely by shifting the mounting position of the shock absorbers 50A and 50B and the sensors 52A and 52B by the dimension corresponding to the altered length. Accordingly, there is no need of providing a calculation step of converting the altered amount of the cutting length into a rotational amount of the brake roller.

The second embodiment of this invention is described with reference to FIG. 12. In the second embodiment, in addition to the shock absorbers 50A and 50B, there is provided a shock absorber 50C at an intermediate position between the shock absorbers 50A and 50B, as intermediate stopper means. Specifically, a block member 120 is fixedly mounted on the rodless cylinder 46, and an expandable rod of an air cylinder 122 is fixedly mounted on the block member 120. The shock absorber 50C is fixedly mounted on a main body of the air cylinder 122.

When the air cylinder 122 is expanded and contracted, as shown in FIG. 12, the shock absorber 50C changes its state between an obstructing state of obstructing the transport motion of the movable block 48 along the transport path and the retracted state in which the shock absorber 50C is retracted away from the transport path. A sensor (intermediate position detector means) 52C is provided at the position at which the movable block 48 comes into contact with the shock absorber 50C to detect that the movable block 48 has reached the position of the shock absorber 50C.

In this embodiment, the controller 51 is changeably set between a first mode and a second mode. When the controller 51 is set to the first mode, transport of the movable block 48 is suspended upon the sensor 52B detecting the presence of the movable block 48 departing from the shock absorber 50A. On the other hand, when the controller 51 is set to the second mode, transport of the movable block 48 is suspended upon the sensor 52C detecting the presence of the movable block 48 departing from the shock absorber 50A.

With this arrangement, when the shock absorber 50C is retracted from the transport path of the movable block 48, and the controller 51 is set to the first mode, automated is the cutting of the suture Y by the length corresponding to the distance L1 between the shock absorbers 50A and 50B. On the other hand, when the shock absorber 50C is moved to the obstructing position on the transport path, and the controller 51 is set to the second mode, automated is the cutting of the suture Y by the length corresponding to the distance L2 between the shock absorbers 50A and 50C. In other words, changing of the control mode can facilitate selection of the cutting lengths, i.e., L1 and L2 without changing the mounting position of the shock absorber and the sensor.

When the controller 51 is set at the second mode, the suture supply device may be operated in the following manner. After the suture Y is cut at the specified cutting length, the shock absorber 50C is retracted from the transport path. Then, the transport/holding device 42 is moved forward to transport the lead end of the cut suture Y to the insertion/holding device 39.

Note that the number of intermediate sensor and intermediate shock absorber is not limited to one. Increasing the number of these elements makes it possible to obtain suture strands of various cutting lengths.

Figure 13:
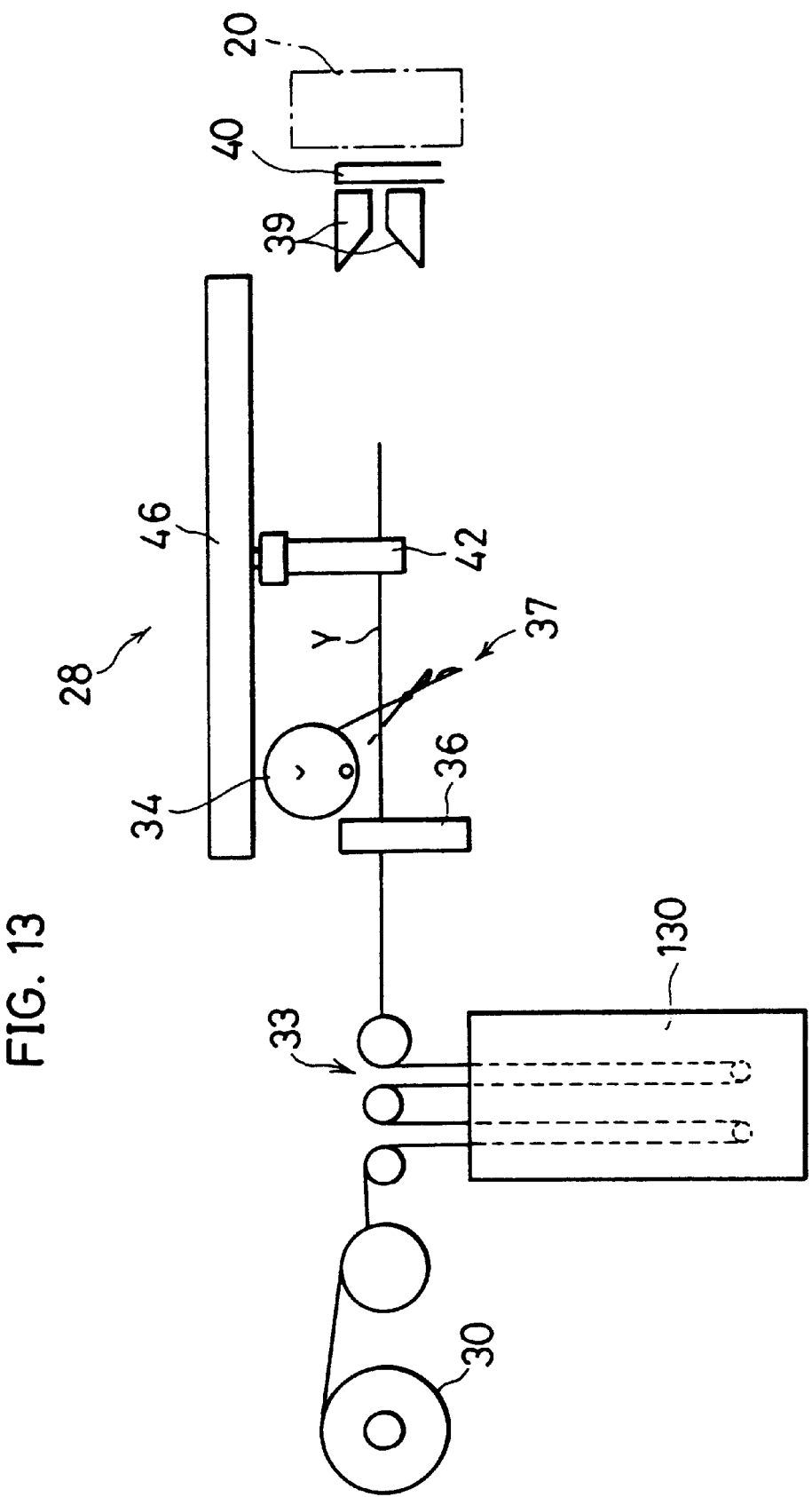
FIG. 13 is a schematic diagram showing an entire arrangement of a suture supply device in a third embodiment.

The third embodiment of this invention is described with reference to FIG. 13.

The needle attached suture manufacturing apparatus shown in the first embodiment is desirable in handling a suture Y mainly composed of multifilament. A suture supply device of the third embodiment shown in FIG. 13 is provided with a heater 130 for correcting a curl of a suture Y to assuredly bond the suture Y composed of monofilament to the needle N. Since the monofilament is free from the spread of an end portion of the suture strand after cutting, the curing agent apply nozzle 43 and the dryer 44 shown in FIG. 3 can be omitted.

Figure 14:
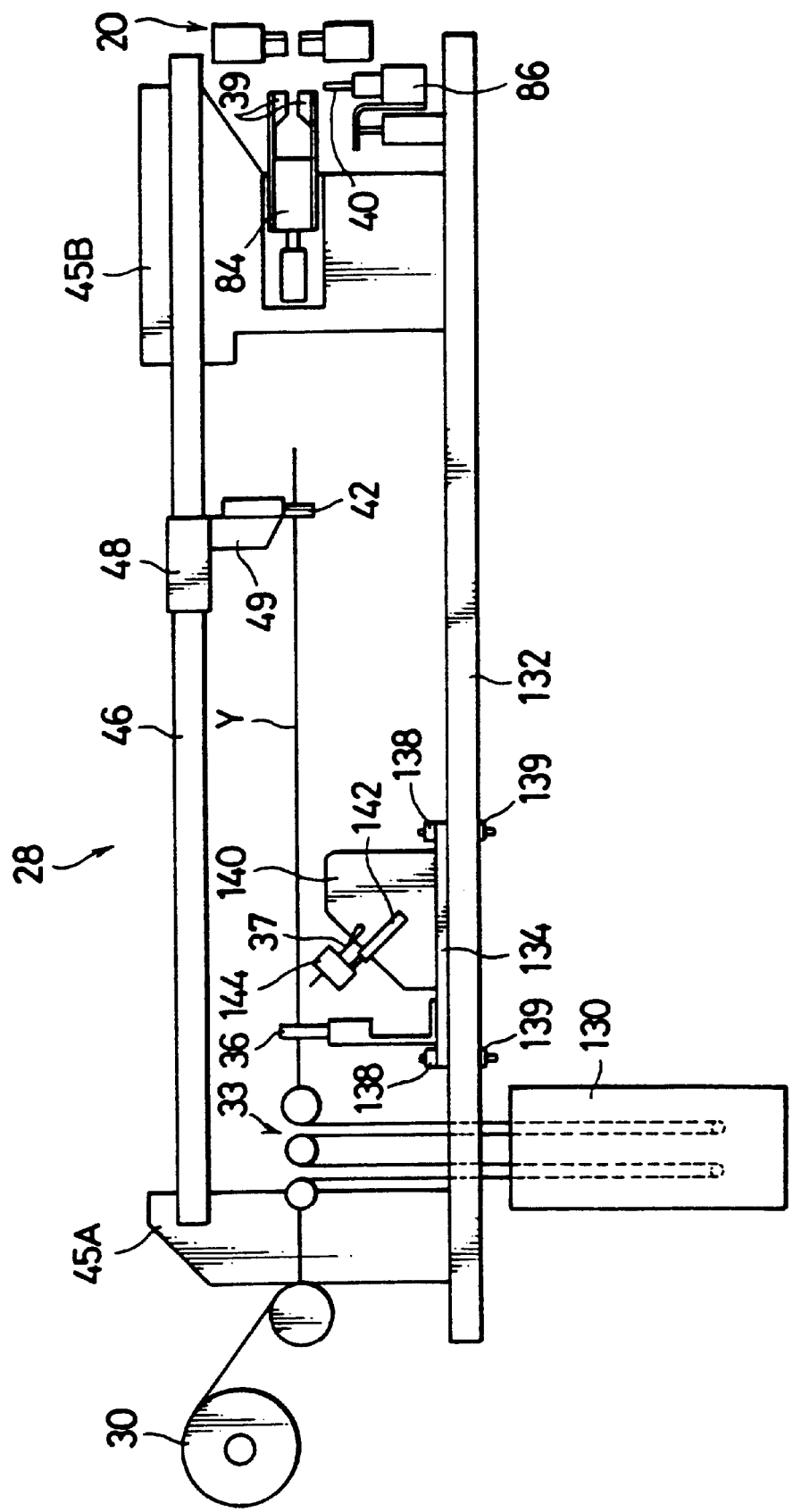
FIG. 14 is a schematic diagram showing an entire arrangement of a suture supply device in a fourth embodiment.

The fourth embodiment of this invention is described with reference to FIGS. 14 and 15.

Similar to the suture supply device shown in the third embodiment, the suture supply device in the fourth embodiment is advantageous in handling a suture of monofilament. Accordingly, the heater 130 is provided, and the curing agent supply nozzle 43 and the dryer 44 are omitted.

In this embodiment, a mounting member 134 for mounting a cutter is provided on a base member 132. A pair of grooves 136, 136 extending in the suture feed direction (left and right direction in FIGS. 14 and 15) are formed in the base member 132. A bolt 138 is inserted in the groove 136 and in a bolt insertion hole of the mounting member 134. The bolt 138 is engaged with a nut 139 at the underside of the base member 132. Thereby, the mounting member 134 can be fixedly attached to the base member 132 at any desired position along the grooves 136, 136. In other words, the cutting position by the cutter 37 can be adjusted at any desired position.

A holding device 36 and a cylinder support wall 140 is mounted on the mounting member 134 in an upright posture. An air cylinder 142 is fixedly mounted on the cylinder support wall 140 obliquely upward. The cutter 37 is connected to the lead end of an expandable rod of the air cylinder 142 via a connecting member 144. With this arrangement, when the air cylinder 142 is expanded and contracted, the cutter 37 is shifted to the cutting position at which the cutter 37 is operable to cut the suture Y and the retracted position at which the cutter 37 is retracted obliquely downward away from the cutting position.

A ruler (measurement device) 146 provided with scale for adjusting the cutting position is arranged on the base member 132 along the extending direction of the groove 136 at a position near the mounting position of the mounting member 134.

In the suture supply device of this embodiment, the cutting position of the cutter 37 can be set to such a position away from the end of the needle N which is held by the needle retaining unit 16 by a predetermined target distance, and the cutter 37 is operable to cut the suture Y after it is confirmed that the insertion/holding device 39 has inserted the lead end of the suture Y in the insertion hole 116 of the needle N. In this case, also, similar to the first to the third embodiments, the cutting length of the suture can be accurately adjusted to the predetermined target length.

In the first to the fourth embodiments, insertion means for inserting the lead end of the suture Y into the insertion hole 116 of the needle is the insertion/nipping device 39, which is provided separately from the transport/holding device 42. Alternatively, the transport/holding device 42 may also be used as the insertion means. The former case, however, is more advantageous in that the transport/holding device 42 can return to the initial position (position between the holding devices 36 and 36 in FIG. 3) during an insertion operation of the suture by the insertion/nipping device 39. Thereby, production efficiency is further improved.

The construction of the insertion means is not limited to the one shown in the above embodiments. For instance, insertion/nipping devices 150A and 150B shown in FIGS. 16 and 17 may be applicable.

Figure 16:
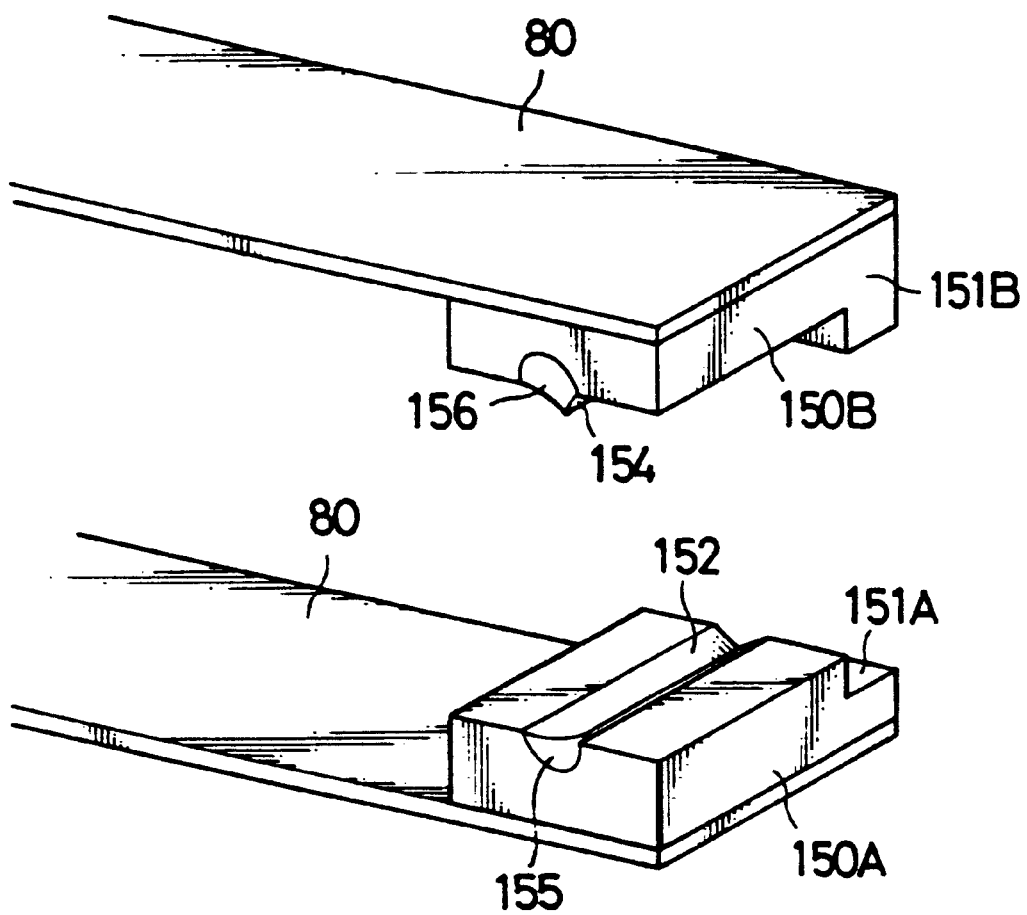
FIG. 16 is a perspective view showing a modification of the insertion/nipping device of this invention.
Figure 17:
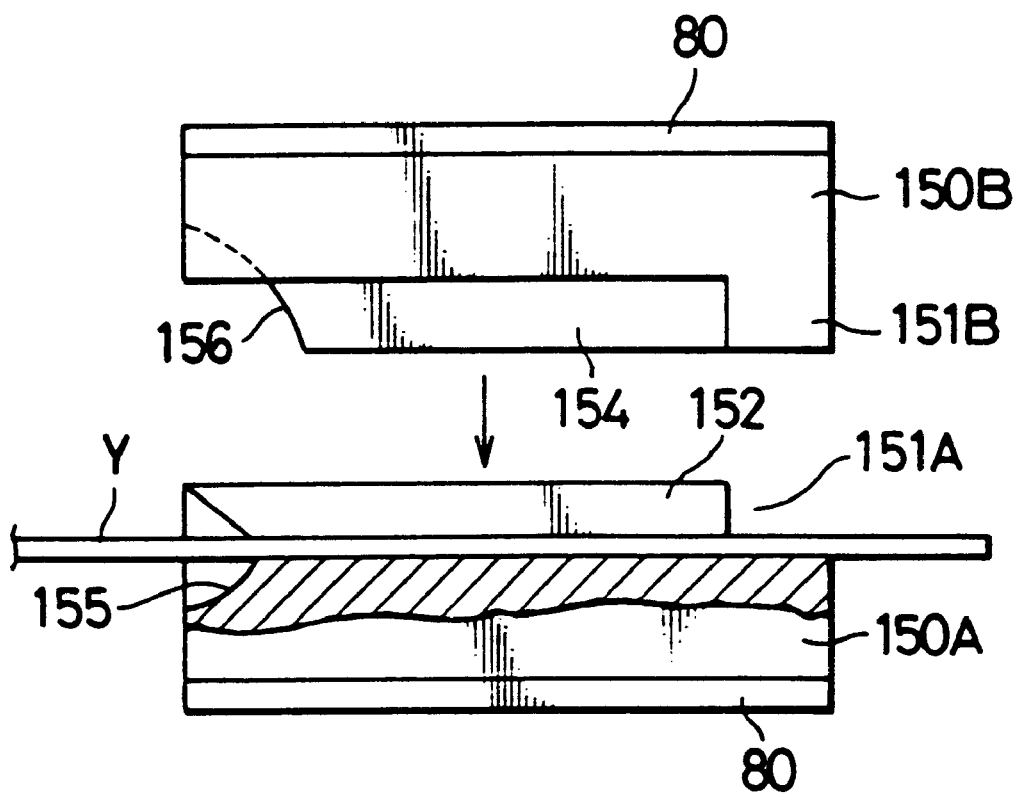
FIG. 17 is a partially cross sectional side view of the insertion/nipping device in FIG. 16.

In FIGS. 16 and 17, the lower insertion/nipping device 150A is formed with a V-shaped groove 152 extending in the suture insertion direction, while the upper insertion/nipping device 150B is formed with a ridge 154 projecting downward at the position corresponding to the V-shaped groove 152. Tapered guide portions 155 and 156 are formed at the suture inlet side (left side in FIG. 17) of the insertion/nipping devices 150A and 150B to guide the lead end of the suture. A stepped portion 151A with the same depth as the V-shaped groove 152 is formed on the suture outlet side (right side in FIG. 17) of the lower insertion/nipping device 150A. A projection wall 151B projecting downward and with the same height as the ridge 154 is formed at the suture outlet side of the upper insertion/nipping device 150B.

According to the arrangement of the insertion/nipping devices 150A and 150B, the suture Y can be held accurately at the center position of the V-shaped groove 152 (at the bottom end). Further, the tapered guide portions 155 and 156 can smoothly guide the insertion of the lead end of the suture Y into the insertion/nipping devices 150A and 150B.

In this way, the insertion means can be freely configured.

In the first embodiment, curing means for curing the suture is the curing agent to be coated on the surface of the suture. Alternatively, the curing agent may be sprayed onto the surface of the suture through a spray type nozzle. This altered method is also effective in desirably performing a curing operation on the suture Y, similar to the embodiment.

EXPLOITATION IN INDUSTRY

As mentioned above, the present invention is effectively applicable, in the field of producing needle attached sutures, to a method for combining a suture of a predetermined length with the end of the needle and an apparatus therefor.

What is claimed is:

1. An apparatus for manufacturing a needle attached suture in which an end of a needle is swaged with a lead end of a suture inserted in an insertion hole formed in the end of the needle to combine the suture with the needle, the apparatus comprises:

a suture winding member for winding the suture;

suture holding means for holding a portion of the suture near the lead end of the suture wound around the suture winding member;

transport means for transporting the suture holding means straight in a suture transport direction toward the insertion hole of the needle by a predetermined distance corresponding to a predetermined target value;

cutting means for cutting the suture at a certain position after the transport means transports the suture holding means by the predetermined distance;

insertion means downstream of the suture holding means for nipping the suture near the lead end of the suture held by the holding means in a first direction orthogonal to said suture transport direction and for further advancing the lead end of the suture to insert the lead end of the suture into said insertion hole of the needle; and center positioning means downstream of the insertion means for nipping the suture near the lead end of the suture from a second direction orthogonal to the first direction.

2. The apparatus according to claim 1, wherein the transport means is constructed such that the predetermined target value is adjustable.

3. The apparatus according to claim 2, wherein the transport means includes reciprocal drive means for reciprocating the suture holding means along a predetermined transport path between two positions; end detector means for detecting the presence of the suture holding means at each position while being transported by the transport means; and transport control means for controlling the transport means to suspend the transport of the suture holding means when the end detector means detects the presence of the suture holding means, the position detected by the end detector means being adjustable.

4. The apparatus according to claim 3, further comprising a stopper for halting the transport of the suture holding means when it is judged that the suture holding means reaches the position detected by the end detector means, and wherein the transport halt position of the stopper is adjustable.

5. The apparatus according to claim 4, further comprising intermediate position detector means for detecting the presence of the suture holding means at an intermediate position between the two positions, and wherein the transport control means is selectable between a first mode and a second mode, the first mode being such that the transport of the suture holding means is suspended when it is judged that the suture holding means reaches the position detected by the end detector means after feeding of the suture is initiated by the suture holding means, the second mode being such that the transport of the suture holding means is suspended when it is judged that the suture holding means reaches the intermediate position detected by the intermediate position detector means after feeding of the suture is initiated by the suture holding means.

6. The apparatus according to claim 5, wherein the suture holding means includes an intermediate stopper for being selectable between a halting position to halt the transport motion of the suture holding means when the suture holding means reaches the intermediate position detected by the intermediate position detector means, and an allowing position to allow the transport motion of the suture holding means along the transport path.

7. The apparatus according to claim 1, wherein the cutting means includes a cutter that cuts the suture obliquely.

8. The apparatus according to claim 7, wherein the cutter is directed obliquely upwardly.

9. The apparatus according to claim 8, wherein the cutting means includes a connecting member which connects the cutter thereto, said cutting means further including a support member, a cylinder mounted on said support member to expand and contract to obliquely move the cutter between a cutting position where the cutter is at a cutting position to cut the suture and a retracted position where the cutter is displaced from the cutting position.

10. The apparatus for manufacturing a needle attached suture in which an end of a needle is swaged with a lead end of a suture inserted in an insertion hole formed in the end of the needle to combine the suture with the needle, the apparatus comprises;

a suture winding member for winding the suture;

suture holding means for holding a portion of the suture near the lead end of the suture wound around the suture winding member;

transport means for transporting the suture holding means straight in a suture transport direction toward the insertion hole of the needle; cutting means for cutting the suture after the lead end of the suture is inserted in the insertion hole of the needle;

insertion means downstream of the suture holding means for nipping the suture near the lead end of the suture held by the holding means in a first direction orthogonal to said suture transport direction and for further advancing the lead end of the suture to insert the lead end of the suture into said insertion hole of the needle; and center positioning means downstream of the insertion means for nipping the suture near the lead end of suture from a second direction orthogonal to the first direction.

11. The apparatus according to claim 10, wherein the cutting means is constructed such that the cutting position is adjustable.

12. The apparatus according to claim 1 or 10, further comprising curing means for curing a region of the suture near the cutting position after feeding of the suture and before cutting of the suture.

13. The apparatus according to claim 12, wherein the curing means includes curing agent applying means for applying a curing agent to the suture, and conveyor means for moving the curing agent applying means in the longitudinal direction of the suture within the curing region.

14. The apparatus according to claim 13, further comprising curing agent dryer means for drying the curing agent applied by the curing agent applying means, and wherein the conveyor means is constructed to move the curing agent applying means and the curing agent dryer means as a unit in the longitudinal direction of the suture.

15. The apparatus according to claim 13, further comprising holding members for holding the suture at plural positions encompassing the curing region after feeding of the suture and before cutting of the suture, and tension supplier means for providing a tension force on the suture in the holding region by the holding members by applying an external force to the suture, and wherein the curing agent applying means is constructed such that the curing agent is applied to the suture while the tension force is applied by the tension supplier.

16. The apparatus according to claim 1 or 10, wherein the insertion means nips the suture held by the suture holding means after the transport means transports the suture holding means to a predetermined position, said insertion means inserting the lead end of the suture in the insertion hole of the needle after the suture holding means releases the holding of the suture, the suture holding means being operable to return to an initial position before the transport by the transport means during an insertion operation by the insertion means.

17. The apparatus according to claim 1 or 10, wherein the first direction is a vertical direction and the second direction is a horizontal direction.

18. An apparatus for manufacturing a needle attached suture comprising:

a suture supply device for supplying a suture having a leading end portion;

a suture holding device for holding the leading end portion of the suture;

a transport device for transporting the suture holding device in a suture transport direction toward an insertion hole in the needle;

a cutting device for cutting the suture after the transport device transports the suture;

an insertion device downstream of said holding device and moveable between an engaged position engaging a leading end portion of said suture and a disengaged position disengaged from said leading end portion of said suture, said insertion device when in said engaged position engaging opposite sides of the leading end portion of the suture;

a positioning device downstream of said holding device having an actuated position in which the positioning device positions the leading end portion of the suture in a predetermined position on said insertion device when said insertion device is in said disengaged position;

said insertion device being changed from said disengaged position to said engaged position after the leading end portion of the suture is in said predetermined position, said insertion device when in the last said engaged position advancing said leading end portion of said suture to insert the leading end of the suture into the insertion hole of the needle.

19. Apparatus according to claim 18 wherein said positioning device is downstream of said insertion device.

20. Apparatus according to claim 18 wherein said insertion device is moveable generally parallel to said suture transport direction between an advanced position and a retracted position, said insertion device when in said advanced position being operable to insert the leading end of said suture into the insertion hole of the needle, said positioning device having a displaced position displaced from said actuated position, said positioning device being moveable in a direction generally transversely of said suture transport direction between said actuated position and said displaced position, said positioning device being in said actuated position when said insertion device is in said retracted position, said positioning device being in said displaced position when said insertion device is in said advanced position.

21. Apparatus according to claim 20 wherein said insertion device is in said engaged position when said insertion device is moved from said retracted to said advanced position.

22. Apparatus according to claim 18 wherein said insertion device includes engageable members having first parallel parts engaging first opposite sides of said leading end portion of said suture when said insertion device is in said engaged position, said positioning device including second engageable parts engaging second opposite sides of said leading end portion of said suture when said positioning device is in said actuated position, said first parallel parts being perpendicular to said second parallel parts when said first and second parallel parts engage said first and second opposite sides respectively of said leading edge portion of said suture.

23. An apparatus for manufacturing a needle threaded suture comprising:

a suture supply device for supplying a suture having a leading end portion;

a suture holding device for holding the leading end portion of the suture;

a transport device for transporting the suture holding device in a generally horizontal suture transport direction toward an insertion hole in the needle;

a cutting device for cutting the suture after the transport device transports the suture;

a curing device upstream of said cutting device for applying a curing agent to a generally horizontal elongated region of the suture before cutting of the suture by said cutting device;

a conveyor device for moving the curing device in the horizontal suture transport direction as the curing device progressively applies said curing agent along said horizontal elongated region of the suture; and an insertion device downstream of said holding device and moveable between an engaged position engaging a leading end portion of said suture and a disengaged position disengaged from said leading end portion of said suture, said insertion device when in said engaged position engaging the leading end portion of the suture to insert the leading end of the suture into the insertion hole of the needle.

24. The apparatus according to claim 23, further comprising a curing agent dryer device for drying the curing agent applied by the curing device, said conveyor device being constructed to move the curing device and the curing agent dryer device as a one-piece unit in the horizontal elongated region of the suture.

25. The apparatus according to claim 23 wherein said curing device includes a discharge nozzle from which said curing agent is discharged onto said elongated region of the suture, said nozzle being substantially in contact with said elongated region of the suture when said discharge nozzle discharges said curing agent onto said elongated region of said suture.

* * * * *